US012378186B2

United States Patent
Wermann et al.

(10) Patent No.: US 12,378,186 B2
(45) Date of Patent: Aug. 5, 2025

(54) INHIBITORS OF MEPRIN α AND β

(71) Applicant: VIVORYON THERAPEUTICS N.V., Halle (DE)

(72) Inventors: Michael Wermann, Halle (DE); Mirko Buchholz, Halle (DE); Hans-Ulrich Demuth, Halle (DE); Daniel Ramsbeck, Halle (DE); Dagmar Schlenzig, Halle (DE); Stephan Schilling, Halle (DE)

(73) Assignee: Vivoryon Therapeutics N.V., Halle (DE)

( * ) Notice: Subject to any disclaimer, the term of this patent is extended or adjusted under 35 U.S.C. 154(b) by 0 days.

(21) Appl. No.: 17/195,391

(22) Filed: Mar. 8, 2021

(65) Prior Publication Data

US 2021/0198189 A1 Jul. 1, 2021

Related U.S. Application Data

(63) Continuation of application No. 16/094,460, filed as application No. PCT/EP2017/059116 on Apr. 18, 2017, now Pat. No. 10,975,019.

(30) Foreign Application Priority Data

Apr. 18, 2016 (EP) ..................................... 16165804

(51) Int. Cl.
| | | |
|---|---|---|
| *C07C 259/06* | (2006.01) | |
| *C07C 255/58* | (2006.01) | |
| *C07D 207/16* | (2006.01) | |
| *C07D 213/36* | (2006.01) | |
| *C07D 317/58* | (2006.01) | |
| *C07D 317/64* | (2006.01) | |
| *C07D 319/18* | (2006.01) | |

(52) U.S. Cl.
CPC .......... *C07C 259/06* (2013.01); *C07C 255/58* (2013.01); *C07D 207/16* (2013.01); *C07D 213/36* (2013.01); *C07D 317/58* (2013.01); *C07D 317/64* (2013.01); *C07D 319/18* (2013.01)

(58) Field of Classification Search
CPC .................................................... C07C 259/06
See application file for complete search history.

(56) References Cited

U.S. PATENT DOCUMENTS

| | | | |
|---|---|---|---|
| 10,975,019 B2 * | 4/2021 | Wermann ................. | A61P 9/12 |
| 2007/0066646 A1 | 3/2007 | Clauzel et al. | |
| 2008/0249181 A1 | 10/2008 | Kohn et al. | |
| 2019/0127317 A1 | 5/2019 | Wermann et al. | |

FOREIGN PATENT DOCUMENTS

| | | | | |
|---|---|---|---|---|
| DE | 10127936 A1 | 12/2001 | | |
| WO | WO-0071514 A1 * | 11/2000 | ........... | C07C 317/48 |
| WO | 2004062601 A2 | 7/2004 | | |
| WO | WO 2008/033745 A2 | 3/2008 | | |
| WO | WO 2008/033745 A3 | 3/2008 | | |
| WO | WO-2009036012 A1 * | 3/2009 | ........... | C07D 261/18 |
| WO | 2015112441 A1 | 7/2015 | | |

OTHER PUBLICATIONS

American Chemical Society. Chemical Abstract Service. RN 2142567-83-5. First entered into STN: Nov. 14, 2017. (Year: 2017).*
American Chemical Society. Chemical Abstract Service. RN 233749-46-7. First entered into STN: Aug. 20, 1999. (Year: 1999).*
International Search Report and Written Opinion mailed Jun. 30, 2017 in connection with PCT/EP2017/059116.
Broder et al., The metalloproteases meprin α and meprin β: unique enzymes in inflammation, neurodegeneration, cancer and fibrosis. Biochem J. Mar. 1, 2013;450(2):253-64. doi: 10.1042/BJ20121751. Review.
Madoux et al., Development of high throughput screening assays and pilot screen for inhibitors of metalloproteases meprin α and β. Biopolymers. Sep. 2014;102(5):396-406. doi: 10.1002/bip.22527.
Ramsbeck et al., Structure-Guided Design, Synthesis, and Characterization of Next-Generation Meprin β Inhibitors. J Med Chem. May 24, 2018;61(10):4578-4592. doi: 10.1021/acs.jmedchem.8b00330. Epub May 7, 2018.
Santos et al., Design, synthesis and molecular modeling study of iminodiacetyl monohydroxamic acid derivatives as MMP inhibitors. Bioorg Med Chem. Nov. 15, 2006;14(22):7539-50. Epub Jul. 27, 2006.
Thompson et al., Structural characterization of three novel hydroxamate-based zinc chelating inhibitors of the Clostridium botulinum serotype A neurotoxin light chain metalloprotease reveals a compact binding site resulting from 60/70 loop flexibility. Biochemistry. May 17, 2011;50(19):4019-28. doi: 10.1021/bi2001483. Epub Apr. 21, 2011.
Thorarensen et al., Identification of novel potent hydroxamic acid inhibitors of peptidyl deformylase and the importance of the hydroxamic acid functionality on inhibition. Bioorg Med Chem Lett. Jun. 4, 2001;11(11):1355-8. Erratum in: Bioorg Med Chem Lett Aug. 6, 2001;11(15):2053.
U.S. Appl. No. 16/094,460, filed Oct. 17, 2018, Wermann et al.
PCT/EP2017/059116, Jun. 30, 2017, International Search Report and Written Opinion.

(Continued)

*Primary Examiner* — John S Kenyon
(74) *Attorney, Agent, or Firm* — Olson & Cepuritis, Ltd.

(57) ABSTRACT

The present invention relates to novel hydroxamic acid derivatives as inhibitors of meprin β and/or α, pharmaceutical compositions comprising such compounds, methods for treatment or prophylaxis of diseases or conditions, especially such that are related to meprin β and/or α, and compounds and pharmaceutical compositions for use in such methods.

19 Claims, No Drawings

Specification includes a Sequence Listing.

(56) References Cited

OTHER PUBLICATIONS

Broder, Claudia et al., The Metalloproteases Meprin α and Meprin β: Unique Enzymes in Inflammation, Neurodegeneration, Cancer and Fibrosis, Biochem. J. 460, 253-264 (2013).

Gu, Xianfeng et al., Design and Evaluation of Hydroxamate Derivatives as Metal-Mediated Inhibitors of A Protein Tyrosine Kinase, J. Med. Chem. 49, 7532-7539 (2006).

Topai, Alessandra et al., In Silico Scaffold Evaluation and Solid Phase Approach to Identify New Gelatinase Inhibitors, Bioorganic & Medicinal Chemistry 20, 2323-2337 (2012).

* cited by examiner

INHIBITORS OF MEPRIN α AND β

CROSS-REFERENCE TO RELATED APPLICATIONS

This Application is a Continuation application of U.S. application Ser. No. 16/094,460, filed Oct. 17, 2018, which is a National Stage filing under 35 U.S.C. 371 of International Patent Application No. PCT/EP2017/059116, filed Apr. 18, 2017, which claims priority to European Application Number 16165804.2, filed Apr. 18, 2016. The entire contents of these applications are incorporated herein by reference in their entirety.

FIELD OF THE INVENTION

The present invention relates to novel hydroxamic acid derivatives as inhibitors of meprin β and/or α, pharmaceutical compositions comprising such compounds, methods for treatment or prophylaxis of diseases or conditions, especially such that are related to meprin β and/or α, and compounds and pharmaceutical compositions for use in such methods.

BACKGROUND ART

Meprin α and β both represent zinc-dependent metalloproteases of the astacin family and the metzincin superfamily. They show a similar domain structure and the human enzymes are of 45% sequence homology to each other. Meprin β is a type 1 transmembrane protein with extracellular protease activity whereas meprin α is shed during the secretory pathway and secreted into extracellular space. Both enzymes are expressed as zymogens with high expression rates in epithelial cells of the kidney and intestine, and they have been demonstrated in intestinal leukocytes, skin and certain cancer cells.

The meprins show distinct substrate specificity with a preference of acidic amino acids in the Pl'-position (Becker-Pauly, C.; Barre, O.; Schilling, O.; auf dem Keller, U.; Ohler, A.; Broder, C. et al. (2011), Mol.Cell Proteomics, doi: 10.1074/mcp. M111.009233). A number of in vitro substrates have been identified including extracellular matrix proteins, peptide hormones and cytokines. Known in vitro substrates of meprin β comprise orcokinin, gastrin 17, Peptide YY, kinetensin, osteopontin, interleukin 1β, APP, MUC 2 mucin, and cystic fibrosis transmembrane conductance regulator E-cadherin, whereas known in vitro substrates of meprin α comprise bombesin, neurotensin, Substance P, angiotensin I, luteinizing hormone releasing hormone, valosin, vasoactive intestinal peptide, bradykinin, α-melanocyte stimulating hormone, MCP-1, and occludin. Known in vitro substrates of both meprin β and α are, e.g., the Gastrin-releasing peptide, and Cholecystokinin.

Although the function of meprins in vivo still remains to be elucidated, there is increasing evidence for their role in collagen assembly, inflammation, intestinal immune response and neurodegeneration.

Meprin β has been shown to act as β-secretase of amyloid precursor protein to form amyloid β (Aβ) peptides in vitro (Bien, Jessica; Jefferson, Tamara; Causevic, Mirsada; Jumpertz, Thorsten; Munter, Lisa; Multhaup, Gerd et al. (2012), The Journal of biological chemistry 287 (40), pp. 33304-33313). The AB peptide, which is abundantly found in the brains of patients suffering from Alzheimer's disease, is central in the pathogenesis of this disease. Said study showed that, in contrast to BACE I, meprin β is capable of formation of N-terminally truncated Aβ and therefore might be involved in the generation of potentially more toxic species of Aβ. Accordingly, meprin β appears to be involved in the pathogenesis and/or disease progression of, e.g., Alzheimer's disease.

The lack of meprin β and α in mouse or the use of Actinonin (a meprin inhibitor) have been shown to protect against renal injury and bladder inflammation (Bylander, John; Li, Qing; Ramesh, Ganesan; Zhang, Binzhi; Reeves, W. Brian; Bond, Judith S. (2008), American journal of physiology. Renal physiology 294 (3), pp. F480-90; Yura, Renee E.; Bradley, S. Gaylen; Ramesh, Ganesan; Reeves, W. Brian; Bond, Judith S. (2009), American journal of physiology. Renal physiology 296 (1), pp. F135-44). Accordingly, meprin β and α appear to be involved in the pathogenesis and/or disease progression of, e.g., nephritis, renal injury, renal ischemic injury, ischemic acute tubular necrosis, acute renal failure, and bladder inflammation.

Both enzymes have been demonstrated to be C- and N-procollagen proteinases and to induce collagen maturation and assembly (Biasin, Valentina; Marsh, Leigh M.; Egemnazarov, Bakytbek; Wilhelm, Jochen; Ghanim, Bahil; Klepetko, Walter et al. (2014), The Journal of pathology 233 (1), pp. 7-17; Prox, Johannes; Arnold, Philipp; Becker-Pauly, Christoph (2015), Matrix biology 44-46, pp. 7-13). Under fibrotic conditions (keloids, pulmonary hypertension), overexpression of the enzymes has been found in these studies. Accordingly, meprin β and α appear be involved in the pathogenesis and/or disease progression of, e.g., fibrosis and fibrotic conditions (keloids, pulmonary hypertension) and interstitial lung disease (ILD).

Meprin o has been shown to be a susceptibility gene for IBD (Crohn's disease, ulcerative colitis) and that its absence increases chronic inflammation, while meprin β has proinflammatory activity and its lack results in some protection from injury (Banerjee, Sanjita; Jin, Ge; Bradley, S. Gaylen; Matters, Gail L.; Gailey, Ryan D.; Crisman, Jacqueline M.; Bond, Judith S. (2011), Am. J. Physiol. Gastrointest. Liver Physiol. 300 (2), pp. G273-82). Accordingly, meprin β and α appear to be involved in the pathogenesis and/or disease progression of, e.g., chronic inflammation, Crohn's disease, ulcerative colitis, and inflammatory bowel disease (IBD).

Pro-angiogenetic activity and non-polarized secretion have been described for meprin α, thereby increasing invasiveness of colorectal cancer (Lottaz, Daniel; Maurer, Christoph A.; Noël, Agnès; Blacher, Silvia; Huguenin, Maya; Nievergelt, Alexandra et al. (2011), Plos one 6 (11), p. e26450). Accordingly, meprin α pathogenesis and/or disease progression of cancer, especially colorectal cancer.

Several broad-spectrum metalloprotease and MMP inhibitors have been elucidated concerning their inhibitory activity towards meprin α and β (Broder, Claudia; Becker-Pauly, Christoph (2013), The Biochemical Journal 450, 253-264). Although some compounds showed inhibition of meprin α, for all the compounds, the inhibition of Meprin β was much lower, (exhibiting inhibition constants in the micromolar range) or were lacking acceptable drug-like properties (Madoux F, Tredup C, Spicer T P, Scampavia L, Chase P S, Hodder P S, Fields G B, Becker-Pauly C, Minond D (2014), Biopolymers 102 (5), pp. 396-406). Broder C., Characterization of the metalloproteases meprin α and meprin β within the protease web (August 2013; Doctoral dissertation; Universitätsbibliothek Kiel; Accession No. urn: nbn: de: gbv: 8-diss-146034; pp. 29, 53) discloses a phosphinic meprin β inhibitor (PMI).

Problems to be Solved by the Invention

In view of the above prior art, the present invention aims, as a main object, to provide potent inhibitors of meprin β and/or α. A first object of the present invention is to provide selective inhibitors of meprin β. A second object of the present invention is to provide selective inhibitors of meprin. A third object of the present invention is to provide dual inhibitors of meprin β and α. A fourth object of the present invention is to provide meprin inhibitors according to any of the aforementioned objects, wherein the inhibitors have acceptable drug-like properties.

A fifth object of the present invention is to provide a pharmaceutical composition comprising a meprin inhibitor according to any of the aforementioned objects that is suitable for administration to a subject in need thereof.

A sixth object of the present is to provide a method for producing the meprin inhibitors according to any of the aforementioned objects.

A seventh object of the present is to provide a method for treatment or prophylaxis of the human or animal body, and a compound or a pharmaceutical composition for use in such a method.

An eight object of the present is to provide a method for treatment or prophylaxis of a subject suffering from or having risk of developing a disease or condition related to meprin β and/or α.

A ninth object of the present is to provide a method for treatment or prophylaxis of a subject suffering from or having risk of developing a disease or condition such as Alzheimer's disease, nephritis, renal injury, renal ischemic injury, ischemic acute tubular necrosis, acute renal failure, bladder inflammation, inflammatory bowel disease (IBD), Crohn's disease, ulcerative colitis, chronic inflammation, colitis, fibrosis, fibrotic conditions, keloids, pulmonary hypertension, or interstitial lung disease (ILD), or cancer, especially colorectal cancer, and/or a compound for use in such a method.

SUMMARY OF THE INVENTION

As a solution to the above-formulated problems, the present invention provides a compound represented by the following Formula I, its individual enantiomers, its individual diastereoisomers, its hydrates, its solvates, its crystal forms, its individual tautomers or a pharmaceutically acceptable salt thereof,

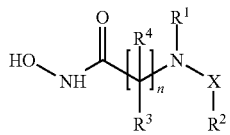

Formula I wherein:
n=1-3, preferably 1 or 2;
$R^1$, $R^3$ and $R^4$ are independently selected from H and the group consisting of alkyl, alkenyl, alkynyl, carbocyclyl, aryl, arylalkyl, heterocyclyl, heteroaryl and heteroarylalkyl, each of which can be optionally substituted;
$R^2$ is selected the group consisting of alkyl, alkenyl, alkynyl, carbocyclyl, aryl, arylalkyl, heterocyclyl, heteroaryl and heteroarylalkyl, each of which is substituted;
wherein any two of $R^1$, $R^2$, $R^3$ and $R^4$ may be joined together to form a ring;
$R^4$ is preferably H;
X is —$CH_2$—.

The present invention also provides a pharmaceutical composition comprising a compound according to above Formula I, its individual enantiomers, its individual diastereoisomers, its hydrates, its solvates, its crystal forms, its individual tautomers or a pharmaceutically acceptable salt thereof; and a pharmaceutically acceptable excipient.

The present invention also provides a method for producing the above compounds.

The present invention also provides a method for treatment or prophylaxis of the human or animal body by surgery or therapy comprising administering a therapeutically effective amount of the above compound or pharmaceutical composition to a subject in need thereof, and/or a compound or pharmaceutical composition for use in such a method.

The present invention also provides a method for treatment or prophylaxis of Alzheimer's disease, nephritis, renal injury, renal ischemic injury, ischemic acute tubular necrosis, acute renal failure, bladder inflammation, inflammatory bowel disease (IBD), Crohn's disease, ulcerative colitis, chronic inflammation, colitis, fibrosis, fibrotic conditions, keloids, pulmonary hypertension, interstitial lung disease (ILD), or cancer, especially colorectal cancer, comprising administering a therapeutically effective amount of the above compound or pharmaceutical composition to a subject in need thereof, and/or a compound or pharmaceutical composition for use in such a method.

DETAILED DESCRIPTION OF THE INVENTION

The term "subject" as used herein, refers to an animal, preferably a mammal, most preferably a human, who is or has been the object of treatment, prophylaxis, observation or experiment.

The term "therapeutically effective amount" as used herein, means that amount of active compound or pharmaceutical agent that elicits the biological or medicinal response in a tissue system, animal or human being sought by a researcher, veterinarian, medical doctor or other clinician, which includes alleviation of the symptoms of the disease or disorder being treated.

The term "alkyl" as used herein, unless specifically limited, denotes a $C_{1-12}$ alkyl group, suitably a $C_{1-8}$ alkyl group, e.g. $C_{1-6}$ alkyl group, e.g. $C_{1-4}$ alkyl group. Alkyl groups may be straight chain or branched. Suitable alkyl groups include, for example, methyl, ethyl, propyl (e.g. n-propyl and isopropyl), butyl (e.g. n-butyl, iso-butyl, sec-butyl and tert-butyl), pentyl (e.g. n-pentyl), hexyl (e.g. n-hexyl), heptyl (e.g. n-heptyl) and octyl (e.g. n-octyl).

The term "alkyl" as used herein also comprises cycloalkyl groups. The expression "cycloalkyl", unless specifically limited, denotes a $C_{3-10}$ cycloalkyl group (i.e. 3 to 10 ring carbon atoms), more suitably a $C_3$-8 cycloalkyl group, e.g. a $C_{3-6}$ cycloalkyl group. Exemplary cycloalkyl groups include cyclopropyl, cyclobutyl, cyclopentyl, cyclohexyl, cycloheptyl and cyclooctyl. A most suitable number of ring carbon atoms is three to six.

The expression "alk", for example in the expressions "alkoxy", "haloalkyl" and "thioalkyl" should be interpreted in accordance with the definition of "alkyl". Exemplary alkoxy groups include methoxy, ethoxy, propoxy (e.g. n-propoxy), butoxy (e.g. n-butoxy), pentoxy (e.g. n-pentoxy), hexoxy (e.g. n-hexoxy), heptoxy (e.g. n-heptoxy) and octoxy (e.g. n-octoxy). Exemplary thioalkyl groups include methylthio. Exemplary haloalkyl groups include fluoroalkyl e.g. $CF_3$; exemplary haloalkoxy groups include fluoroalkyl e.g. $OCF_3$. The expressions "fluoro ($C_{1-6}$ alkyl)" and "fluoro (C$_{1-6}$ alkoxy)" denote a C$_{1-6}$ alkyl and C$_{1-6}$ alkoxy group, respectively, each of which is substituted by one or more fluoro atoms.

The expression "alkenyl", unless specifically limited, denotes a C$_{2-12}$ alkenyl group, suitably a C$_{2-6}$ alkenyl group, e.g. a C$_{2-4}$ alkenyl group, which contains at least one double bond at any desired location and which does not contain any triple bonds. Alkenyl groups may be straight chain or branched. Exemplary alkenyl groups including one double bond include propenyl and butenyl. Exemplary alkenyl groups including two double bonds include pentadienyl, e.g. (1 E, 3E)-pentadienyl.

The expression "alkenyl" as used herein also comprises cycloalkenyl groups. The expression "cycloalkenyl", unless specifically limited, denotes a C$_{5-10}$ cycloalkenyl group (i.e. 5 to 10 ring carbon atoms), more suitably a C$_{3-6}$ cycloalkenyl group e.g. a C$_{5-6}$ cycloalkenyl group. Exemplary cycloalkenyl groups include cyclopropenyl, cyclohexenyl, cycloheptenyl and cyclooctenyl. A most suitable number of ring carbon atoms is five to six.

The expression "alkynyl", unless specifically limited, denotes a C$_{2-12}$ alkynyl group, suitably a C$_{2-6}$ alkynyl group, e.g. a C$_{2-4}$ alkynyl group, which contains at least one triple bond at any desired location and may or may not also contain one or more double bonds. Alkynyl groups may be straight chain or branched. Exemplary alkynyl groups include propynyl and butynyl.

The expression "alkylene" denotes a chain of formula —(CH$_2$)$_n$—wherein n is an integer e.g. 2-5, unless specifically limited.

The expression "carbocyclyl", unless specifically limited, denotes any ring system in which all the ring atoms are carbon and which contains between three and twelve ring carbon atoms, suitably between three and ten carbon atoms and more suitably between three and eight carbon atoms. Carbocyclyl groups may be saturated or partially unsaturated, but do not include aromatic rings. Examples of carbocyclyl groups include monocyclic, bicyclic, and tricyclic ring systems, in particular monocyclic and bicyclic ring systems. Other carbocylcyl groups include bridged ring systems (e.g. bicyclo[2.2.1]heptenyl). A specific example of a carbocyclyl group is a cycloalkyl group. A further example of a carbocyclyl group is a cycloalkenyl group.

The expression "aryl", unless specifically limited, denotes a C$_{6-12}$ aryl group, suitably a C$_{6-10}$ aryl group, more suitably a C$_{6-8}$ aryl group. Aryl groups will contain at least one aromatic ring (e.g. one, two or three rings). An example of a typical aryl group with one aromatic ring is phenyl. An example of a typical aryl group with two aromatic rings is naphthyl.

The expression "arylalkyl", unless specifically limited, denotes an aryl residue which is connected via an alkylene moiety, e.g., a C$_{1-4}$ alkylene moiety.

The expression "heterocyclyl", unless specifically limited, refers to a carbocyclyl group wherein one or more (e.g. 1, 2 or 3) ring atoms are replaced by heteroatoms selected from N, S and O. A specific example of a heterocyclyl group is a cycloalkyl group (e.g. cyclopentyl or more particularly cyclohexyl) wherein one or more (e.g. 1, 2 or 3, particularly 1 or 2, especially 1) ring atoms are replaced by heteroatoms selected from N, S or O. Exemplary heterocyclyl groups containing one hetero atom include pyrrolidine, tetrahydrofuran and piperidine, and exemplary heterocyclyl groups containing two hetero atoms include morpholine and piperazine. A further specific example of a heterocyclyl group is a cycloalkenyl group (e.g. a cyclohexenyl group) wherein one or more (e.g. 1, 2 or 3, particularly 1 or 2, especially 1) ring atoms are replaced by heteroatoms selected from N, S and O. An example of such a group is dihydropyranyl (e.g. 3,4-dihydro-2H-pyran-2-yl-).

The expression "heteroaryl", unless specifically limited, denotes an aryl residue, wherein one or more (e.g. 1, 2, 3, or 4, suitably 1, 2 or 3) ring atoms are replaced by heteroatoms selected from N, S and O, or else a 5-membered aromatic ring containing one or more (e.g. 1, 2, 3, or 4, suitably 1, 2 or 3) ring atoms selected from N, S and O. Exemplary monocyclic heteroaryl groups having one heteroatom include: five membered rings (e.g. pyrrole, furan, thiophene); and six membered rings (e.g. pyridine, such as pyridin-2-yl, pyridin-3-yl and pyridin-4-yl). Exemplary monocyclic heteroaryl groups having two heteroatoms include: five membered rings (e.g. pyrazole, oxazole, isoxazole, thiazole, isothiazole, imidazole, such as imidazol-1-yl, imidazol-2-yl imidazol-4-yl); six membered rings (e.g. pyridazine, pyrimidine, pyrazine). Exemplary monocyclic heteroaryl groups having three heteroatoms include: 1, 2, 3-triazole and 1, 2, 4-triazole. Exemplary monocyclic heteroaryl groups having four heteroatoms include tetrazole. Exemplary bicyclic heteroaryl groups include: indole (e.g. indol-6-yl), benzofuran, benzthiophene, quinoline, isoquinoline, indazole, benzimidazole, benzthiazole, quinazoline and purine.

The expression "heteroarylalkyl", unless specifically limited, denotes a heteroaryl residue which is connected via an alkylene moiety e.g. a C$_{1-4}$ alkylene moiety.

The term "halogen" or "halo" comprises fluorine (F), chlorine (CI) and bromine (Br).

The term "amino" refers to the group —NH$_2$.

The terms "optionally substituted" and "substituted" refer to (optional) substitution by one or several groups independently selected from a halogen atom, a cyano group, a hydroxyl group and a carboxyl group. These terms also refer to (optional) substitution by one or several groups independently selected from —C(O)—O—(C$_{1-6}$ alkyl) group, a —C(O)—NH$_2$ group, a C$_{1-6}$ alkylsulfono group, C$_{1-6}$ alkoxy and a C$_{1-6}$ aliphatic, aromatic or heterocyclic group, each of which may be further substituted by one or several halogen atoms, carboxyl, cyano, and/or hydroxyl groups. Preferably, an alkyl group which is substituted does not have a keto group on the C atom that is directly bound to the N atom in Formula I.

The expressions "alkoxyaryl", "carboxyaryl", "cyanoaryl", "haloaryl", "hydroxyaryl" and "heteroarylaryl", unless specifically limited, denote an aryl residue which is substituted by at least one alkoxy, carboxy, cyano, halo, hydroxy and heteroaryl group, respectively.

The expressions "alkoxyheteroaryl", "carboxyheteroaryl", "cyanoheteroaryl", "haloheteroaryl" and "hydroxyheteroaryl", unless specifically limited, denote a heteroaryl residue which is substituted by at least one alkoxy, carboxy, cyano, halo, and hydroxy group, respectively.

The expression "arylmethyl", unless specifically limited, denotes an aryl residue which is connected via a methylene moiety.

The expressions "(alkoxyaryl)methyl", "(hydroxyaryl)methyl", "(carboxyaryl)methyl", "(heteroarylaryl)methyl" "(alkoxyheteroaryl)methyl", "(hydroxyheteroaryl)methyl" and "(carboxyheteroaryl)methyl", unless specifically limited, denote an alkoxyaryl, hydroxyaryl, carboxyaryl, heteroarylaryl, alkoxyheteroaryl, hydroxyheteroaryl and carboxyheteroaryl residue, respectively, which is connected via a methylene moiety.

Stereoisomers:

All possible stereoisomers of the claimed compounds are included in the present invention.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Preparation and Isolation of Stereoisomers:

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base, or by salt formation with an optically active base, such as quinine, quinidine, quinotoxine, cinkotoxine, (S)-phenylethylamine, (1R, 2S)-ephedrine, (R)-phenylglycinol, (S)-2-aminobutanol, followed by fractional crystallization and regeneration of the free acid. The compounds may also be resolved by formation of diastereomeric esters or amides, followed by chromatographic separation and removal of the chiral auxiliary. Alternatively, the compounds may be resolved using a chiral HPLC column.

Polymorph Crystal Forms:

Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention. The compounds, including their salts, can also be obtained in the form of their hydrates, or include other solvents used for their crystallization.

As used herein, the term "tautomer" refers to the migration of protons between adjacent single and double bonds. The tautomerization process is reversible. Compounds described herein can undergo any possible tautomerization that is within the physical characteristics of the compound.

As used herein, the term "pharmaceutically acceptable" embraces both human and veterinary use. For example, the term "pharmaceutically acceptable" embraces a veterinarily acceptable compound or a compound acceptable in human medicine and health care.

Pharmaceutically Acceptable Salts:

In view of the close relationship between the free compounds and the compounds in the form of their salts, hydrates or solvates, whenever a compound is referred to in this context, a corresponding salt, solvate or polymorph is also intended, provided such is possible or appropriate under the circumstances.

Salts, hydrates and solvates of the compounds of Formula I and physiologically functional derivatives thereof which are suitable for use in medicine are those wherein the counter-ion or associated solvent is pharmaceutically acceptable. However, salts, hydrates and solvates having non-pharmaceutically acceptable counter-ions or associated solvents are within the scope of the present invention, for example, for use as intermediates in the preparation of other compounds and their pharmaceutically acceptable salts, hydrates and solvates.

Suitable salts according to the invention include those formed with both organic and inorganic acids or bases. Pharmaceutically acceptable acid addition salts include those formed from hydrochloric, hydrobromic, sulfuric, nitric, citric, tartaric, phosphoric, lactic, pyruvic, acetic, trifluoroacetic, triphenylacetic, sulfamic, sulfanilic, succinic, oxalic, fumaric, maleic, malic, mandelic, glutamic, aspartic, oxaloacetic, methanesulfonic, ethanesulfonic, arylsulfonic (for example p-toluenesulfonic, benzenesulfonic, naphthalenesulfonic or naphthalenedisulfonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalenes-acrylic), benzoic, 4-methoxybenzoic, 2- or 4-hydroxybenzoic, 4-chlorobenzoic, 4-phenylbenzoic, benzeneacrylic (for example 1, 4-benzenediacrylic), isethionic acids, perchloric, propionic, glycolic, hydroxyethanesulfonic, pamoic, cyclohexanesulfamic, salicylic, saccharinic and trifluoroacetic acid. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glucamine.

All pharmaceutically acceptable acid addition salt forms of the compounds of the present invention are intended to be embraced by the scope of this invention.

Prodrugs:

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985.

As used herein, the term "composition" is intended to encompass a product comprising the claimed compounds in the therapeutically effective amounts, as well as any product which results, directly or indirectly, from combinations of the claimed compounds.

Excipients (Carriers and additives for galenic formulations):

Thus, for liquid oral preparations, such as for example, suspensions, elixirs and solutions, suitable carriers and additives may advantageously include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like.

Carriers, which can be added to the mixture, include necessary and inert pharmaceutical excipients, including, but not limited to, suitable binders, suspending agents, lubricants, flavorants, sweeteners, preservatives, coatings, disintegrating agents, dyes and coloring agents.

Soluble polymers as targetable drug carriers can include polyvinylpyrrolidone, pyran copolymer, polyhydroxypropylmethacrylamidephenol, polyhydroxyethylaspartamide-phenol, or polyethyleneoxidepolylysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like.

Disintegrators include, without limitation, starch, methyl cellulose, agar, bentonite, xanthan gum and the like.

Protective Groups:

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, fully incorporated herein by reference. The protecting groups may be removed at a convenient subsequent stage using methods known from the art.

A protecting group or protective group is introduced into a molecule by chemical modification of a functional group in order to obtain chemoselectivity in a subsequent chemical reaction. Protecting groups are e.g. alcohol protecting groups, amine protecting groups, carbonyl protecting groups, carboxylic acid protecting groups and phosphate protecting groups.

Examples for alcohol protecting groups are acetyl(Ac), benzoyl(Bz), benzyl(Bn, Bnl) β-methoxyethoxymethyl ether (MEM), mimethoxytrityl[bis-(4-methoxyphenyl)phenylmethyl, DMT], methoxymethyl ether (MOM), methoxytrityl[(4-methoxyphenyl)diphenylmethyl, MMT), p-methoxybenzyl ether (PMB), methylthiomethyl ether, pivaloyl(Piv), tetrahydropyranyl (THP), trityl(triphenylmethyl, Tr), silyl ethers (such as trimethylsilyl ether (TMS), tert-butyldimethylsilyl ether (TBDMS), tert-butyldimethylsilyloxymethyl ether (TOM), and triisopropylsilyl ether (TIPS)); methyl ethers and ethoxyethyl ethers (EE).

Suitable amine protecting groups are selected from carbobenzyloxy (Cbz), p-methoxybenzyl carbonyl(Moz or MeOZ), ie f-butyloxycarbonyl (BOC), 9-fluorenylmethyloxycarbonyl (FMOC), acetyl(Ac), benzoyl(Bz), benzyl (Bn), p-methoxybenzyl (PMB), 3, 4-dimethoxybenzyl (DMPM), p-methoxyphenyl (PMP), tosyl(Ts), and other sulfonamides (Nosyl & Nps).

Suitable carbonyl protecting groups are selected from acetals and ketals, acylals and dithianes.

Suitable carboxylic acid protecting groups are selected from methyl esters, benzyl esters, tert-butyl esters, silyl esters, orthoesters, and oxazoline.

Examples for phosphate protecting groups are 2-cyanoethyl and methyl(Me)

Compounds of Formula I

According to aspect 1, the present invention provides a compound represented by the following Formula I, its individual enantiomers, its individual diastereoisomers, its hydrates, its solvates, its crystal forms, its individual tautomers or a pharmaceutically acceptable salt thereof,

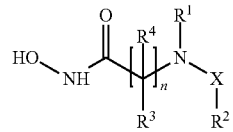

Formula I wherein:
n=1-3, preferably 1 or 2;
$R^1$, $R^3$ and $R^4$ are independently selected from H and the group consisting of alkyl, aryl, arylalkyl, heteroaryl and heteroarylalkyl, each of which can be optionally substituted;
$R^2$ is selected the group consisting of alkyl, aryl, arylalkyl, heteroaryl and heteroarylalkyl, each of which can be optionally, and preferably is substituted;
wherein any two of $R^1$, $R^2$, $R^3$ and $R^4$ may be joined together to form a ring;
$R^4$ is preferably H;
X is —CH$_2$—.

According to an alternative embodiment of this aspect, $R^3$ and $R^4$ are preferably the same, and are more preferably joined together to form a carbocyclic or heterocyclic ring. $R^3$ is preferably H or is preferably selected from the group consisting of $C_{1-6}$ alkyl, aryl, arylalkyl, heteroaryl and heteroarylalkyl, each of which can be optionally substituted; and more preferably selected from the group consisting of methyl, ethyl, 1-propyl, 2-propyl, benzyl, phenyl carboxymethyl and 2-carboxyethyl. In one preferred embodiment of this aspect, n=2. In another preferred embodiment of this aspect, n=3. Most preferably, n=1.

According to aspect 2, the present invention provides the compound according to aspect 1, wherein $R^3$ is H.

According to aspect 3, the present invention provides the compound according to any of aspects 1-2, wherein $R^1$ and $R^3$ are H.

According to aspect 4, the present invention provides the compound according to any of aspects 1-3, wherein $R^1$ is selected from the group consisting of arylmethyl, (alkoxyaryl)methyl, (hydroxyaryl)methyl, (carboxyaryl)methyl, (alkoxyheteroaryl)methyl, (heteroarylaryl)methyl, (hydroxyheteroaryl)methyl and (carboxyheteroaryl)methyl, each of which can be optionally substituted.

According to aspect 5, the present invention provides the compound according to any of aspects 1-4, wherein $R^1$ is represented by the following formula,

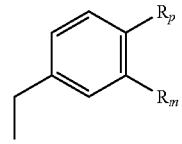

wherein:
(i) at least one of $R_p$ and $R_m$, preferably $R_m$, is a functional group having an acidic hydrogen and is optionally selected from —COOH, -SO$_3$H, -P(O)(OH)$_2$, -C(O)—NH—OH, -OH and tetrazol-5-yl; or (ii) $R_p$ and $R_m$ are alkoxy groups that are joined together as a part of a 5- to 8-membered heterocycle; or (iii) at least one of $R_p$ and $R_m$ is selected from the group consisting of $C_{1-6}$ alkyl, $C_{1-6}$ alkoxy, fluoro ($C_{1-6}$ alkyl), fluoro ($C_{1-6}$ alkoxy), —C(O)—NH$_2$, -C(O)—OCH$_3$, -C(O)—OCH$_2$CH$_3$, fluoro, chloro, bromo, iodo and cyano;

whereby $R^1$ can be optionally further substituted.

According to aspect 6, the present invention provides the compound according to any of aspects 1-5, wherein $R^1$ is selected from the group consisting of (1, 3-benzodioxol-5-yl)methyl, (3-carboxyphenyl)methyl, (4-carboxyphenyl)methyl, (2, 4-difluoro-3-hydroxy-phenyl)-methyl, (3,5-difluoro-4-hydroxy-phenyl methyl, (2,6-difluoro-3-hydroxy-phenyl)methyl, (4-fluoro-3-hydroxy-phenyl)methyl, (2-fluoro-3-hydroxy-phenyl)methyl, (4-chloro-2-fluoro-3-hydroxy-phenyl)-methyl, (4-chloro-2-fluoro-3-methoxyphenyl)-methyl, (2, 4-difluoro-3-methoxy-phenyl)methyl, (3-ethoxycarbonylphenyl)methyl, (4-chloro-2-fluoro-phenyl)methyl, (3, 4, 5-trimethoxyphenyl)methyl, 2,3-dihydro-1, 4-benzodioxin-6-yl-methyl, (7-methoxy-1, 3-benzodioxol-5-yl)methyl and [3-(difluoromethoxy)phenyl]methyl; preferably selected from (3-carboxyphenyl)methyl, 2, 4-difluoro-3-hydroxy-phenyl)-methyl, (4-chloro-2-fluoro-3-hydroxy-phenyl)-methyl and 1, 3-benzodioxol-5-ylmethyl.

According to aspect 7, the present invention provides the compound according to any of aspects 1-6, wherein $R^2$ is selected from the group consisting of aryl, alkoxyaryl, carboxyaryl, cyanoaryl, haloaryl, hydroxyaryl, alkoxyheteroaryl, cyanoheteroaryl, haloheteroaryl, heteroarylaryl, hydroxyheteroaryl and carboxyheteroaryl, each of which can be optionally substituted.

According to aspect 8, the present invention provides the compound according to any of aspects 1-7, wherein $R^2$ is represented by the following formula,

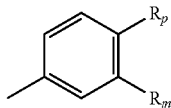

wherein:
(i) at least one of $R_p$ and $R_m$, preferably $R_m$, is a functional group having an acidic hydrogen and is optionally selected from —COOH, -SO$_3$H, -P(O)(OH)$_2$, -C(O)—NH—OH, -OH and tetrazol-5-yl; or (ii) $R_p$ and $R_m$ are alkoxy groups that are joined together as a part of a 5- to 8-membered heterocycle; or (iii) at least one of $R_p$ and $R_m$ is selected from the group
(iii) consisting of $C_{1-6}$ alkyl, $C_{1-6}$ alkoxy, -C(O)—NH$_2$, -C(O)—OCH$_3$, -C(O)—OCH$_2$CH$_3$, fluoro ($C_{1-6}$ alkyl), fluoro ($C_{1-6}$ alkoxy), fluoro, chloro, bromo, iodo and cyano;

whereby $R^2$ can be optionally further substituted.

According to aspect 9, the present invention provides the compound according to any of aspects 1-8, wherein $R^2$ is selected from the group consisting of 1, 3-benzodioxol-5-yl, 3-carboxyphenyl, 1, 3-benzodioxol-5-yl, 3-carboxyphenyl, 4-carboxyphenyl, 3-carboxy-4-methoxyphenyl, 3, 5-dichloro-4-hydroxyphenyl, 4-chlorophenyl, 4-cyanophenyl, 4-fluorophenyl, 2,6-difluoro-4-methoxyphenyl, 3-fluoro-4-methoxyphenyl, 3-methoxyphenyl, 4-methoxyphenyl, 4-chlorophenyl, 4-methylphenyl, 2,4-difluoro-3-hydroxy-phenyl, 3, 5-difluoro-4-hydroxy-phenyl, 2, 6-difluoro-3-hydroxy-phenyl, 4-fluoro-3-hydroxy-phenyl, 2-fluoro-3-hydroxy-phenyl, 4-chloro-2-fluoro-3-hydroxy-phenyl, 4-chloro-2-fluoro-3-methoxy-phenyl, 2, 4-difluoro-3-methoxy-phenyl, 3-ethoxycarbonylphenyl, 4-chloro-2-fluoro-phenyl, 3, 4, 5-trimethoxyphenyl 2, 3-dihydro-1, 4-benzodioxin-6-yl, 7-methoxy-1, 3-benzodioxol-5-yl, 2, 4-difluoro-3-hydroxy-phenyl and 1, 3-benzodioxol-5-yl; preferably preferably selected from 3-carboxyphenyl, 2, 4-difluoro-3-hydroxy-phenyl, 4-chloro-2-fluoro-3-hydroxy-phenyl and 1, 3-benzodioxol-5-yl.

According to aspect 10, the present invention provides the compound according to any of aspects 1-9, wherein:
(i) $R^1$ is (3-carboxyphenyl)methyl and $R^3$ is H;
(ii) $R^2$ is 3-carboxyphenyl and $R^3$ is H;
(iii) $R^1$ is (3-carboxyphenyl)methyl and $R^3$ and $R^4$ are H; or
(iv) $R^2$ is 3-carboxyphenyl and $R^3$ and $R^4$ are H; or
(v) $R^1$ is (2, 4-difluoro-3-hydroxy-phenyl)methyl and $R^2$ 2, 4-difluoro-3-hydroxy-phenyl.

Compounds of Formula V (Series 4)
According to aspect 11, the present invention provides a compound of Formula V:

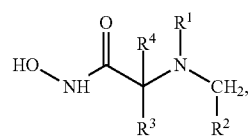

Formula V wherein $R^1$, $R^2$, $R^3$ and $R^4$ are defined as with respect to the above Formula I, with the proviso that $R^1$ is not H. In an alternative embodiment of this aspect, $R^1$ can be H.

According to aspect 12, the present invention provides the compound according to aspect 11, wherein $R^3$ is H.

According to aspect 13, the present invention provides the compound according to aspects 11-12, wherein $R^3$ and $R^4$ are H.

According to aspect 14, the present invention provides the compound according to any of aspects 11-13, wherein $R^1$ is selected from the group consisting of arylmethyl, (alkoxyaryl)methyl, (hydroxyaryl)methyl, (carboxyaryl)methyl, (alkoxyheteroaryl)methyl, (heteroarylaryl)methyl, (hydroxyheteroaryl)methyl and (carboxyheteroaryl)methyl, each of which can be optionally substituted.

According to aspect 15, the present invention provides the compound according to any of aspects 11-14, wherein $R^1$ is represented by the following formula,

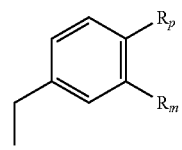

wherein:
(i) at least one of $R_p$ and $R_m$, preferably $R_m$, is a functional group having an acidic hydrogen and is optionally selected from —COOH, -SO$_3$H, -P(O)(OH)$_2$, -C(O)—NH—OH, -OH and tetrazol-5-yl; or (ii) $R_p$ and $R_m$ are alkoxy groups that are joined together as a part of a 5- to 8-membered heterocycle, whereby $R^1$ can be optionally further substituted.

According to aspect 16, the present invention provides the compound according to any of aspects 11-15, wherein $R^1$ is selected from the group consisting of (1, 3-benzodioxol-5-yl)methyl, (3-carboxyphenyl methyl, and (4-carboxyphenyl)methyl; preferably (3-carboxyphenyl)methyl.

According to aspect 17, the present invention provides the compound according to any of aspects 11-16, wherein $R^2$ is selected from the group consisting of aryl, alkoxyaryl, carboxyaryl, cyanoaryl, haloaryl, hydroxyaryl, alkoxyheteroaryl, cyanoheteroaryl, haloheteroaryl, heteroarylaryl, hydroxyheteroaryl and carboxyheteroaryl, each of which can be optionally substituted.

According to aspect 45, the present invention provides the compound according to any of aspects 38-44, wherein $R^2$ is represented by the following formula,

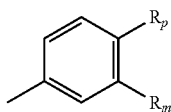

wherein:
(i) at least one of $R_p$ and $R_m$, preferably $R_m$, is a functional group having an acidic hydrogen and is optionally selected from —COOH, -SO$_3$H, -P(O)(OH)$_2$, -C(O)—NH—OH, -OH and tetrazol-5-yl; or
(ii) $R_p$ and $R_m$ are alkoxy groups that are joined together as a part of a 5- to 8-membered heterocycle; or
(iii) at least one of $R_p$ and $R_m$ is selected from the group consisting of $C_{1-6}$ alkyl, $C_{1-6}$ alkoxy, fluoro ($C_{1-6}$ alkyl), fluoro ($C_{1-6}$ alkoxy), fluoro, chloro, bromo, iodo and cyano;
whereby $R^2$ can be optionally further substituted.

According to aspect 18, the present invention provides the compound according to any of aspects 11-17, wherein $R^2$ is selected from the group consisting of 1, 3-benzodioxol-5-yl, 3-carboxyphenyl, 1,3-benzodioxol-5-yl, 3-carboxyphenyl, 4-carboxyphenyl, 3-carboxy-4-methoxyphenyl, 3, 5-dichloro-4-hydroxyphenyl, 4-chlorophenyl, 4-cyanophenyl, 4-fluorophenyl, 2, 6-difluoro-4-methoxyphenyl, 3-fluoro-4-methoxyphenyl, 3-methoxyphenyl, 4-methoxyphenyl, 4-chlorophenyl, and 4-methylphenyl.

According to aspect 19, the present invention provides the compound according to any of aspects 11-18, wherein:
(i) $R^1$ is (3-carboxyphenyl)methyl and $R^3$ is H;
(ii) $R^2$ is 3-carboxyphenyl and $R^3$ is H
(iii) $R^1$ is (3-carboxyphenyl)methyl, and $R^3$ and $R^4$ are H; or
(iv) $R^2$ is 3-carboxyphenyl, and $R^3$ and $R^4$ are H.

Individual Compounds

According to aspect 20, the compound according to the present invention is most preferably selected from the group consisting of:

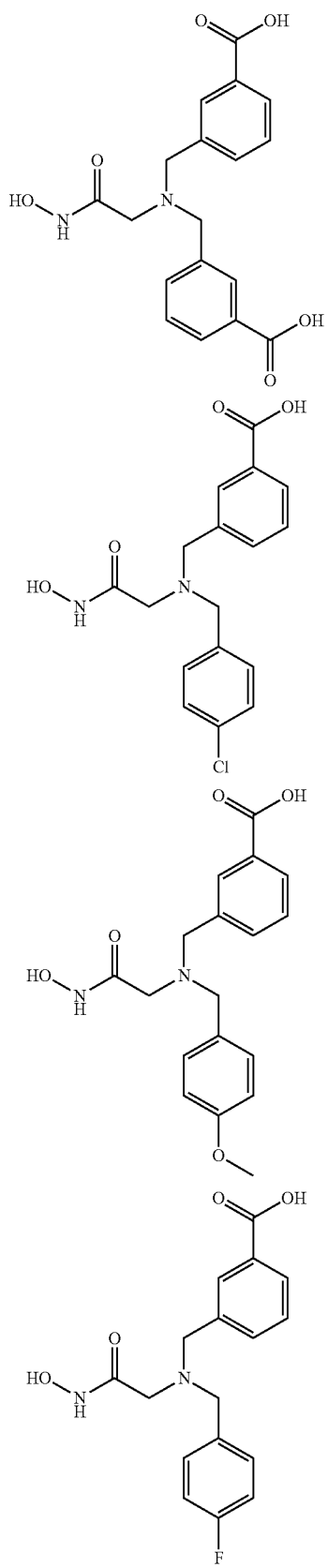

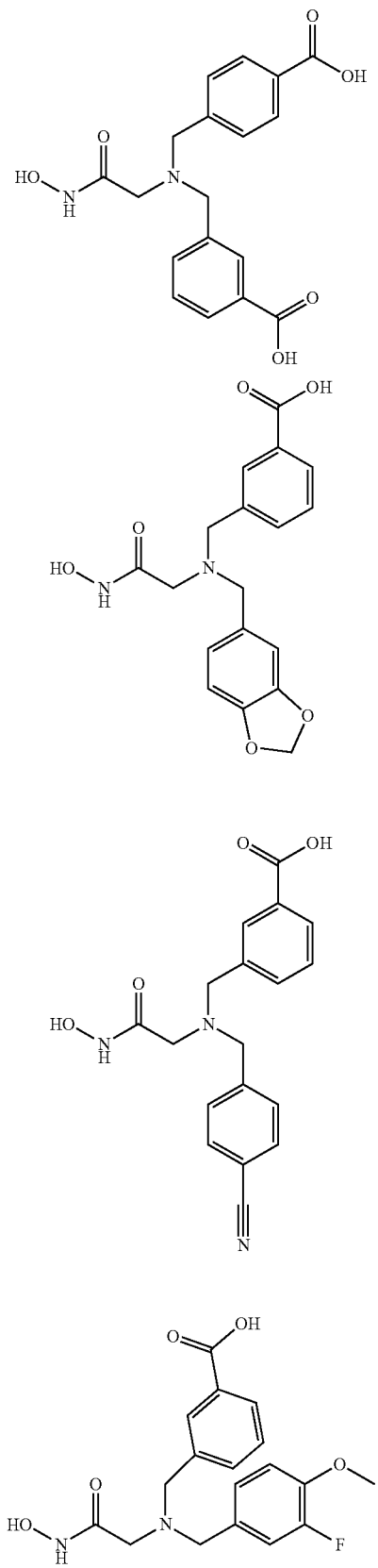
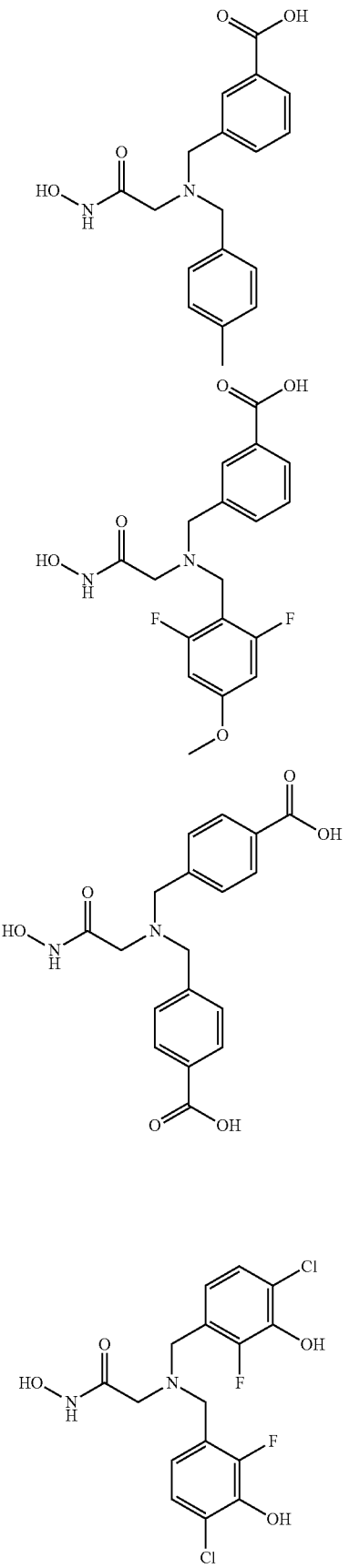

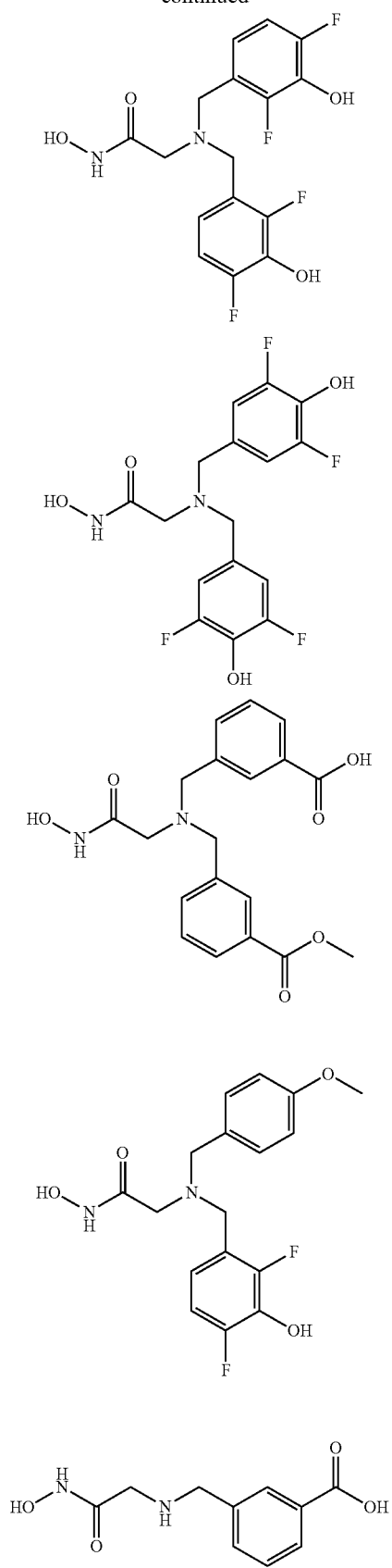
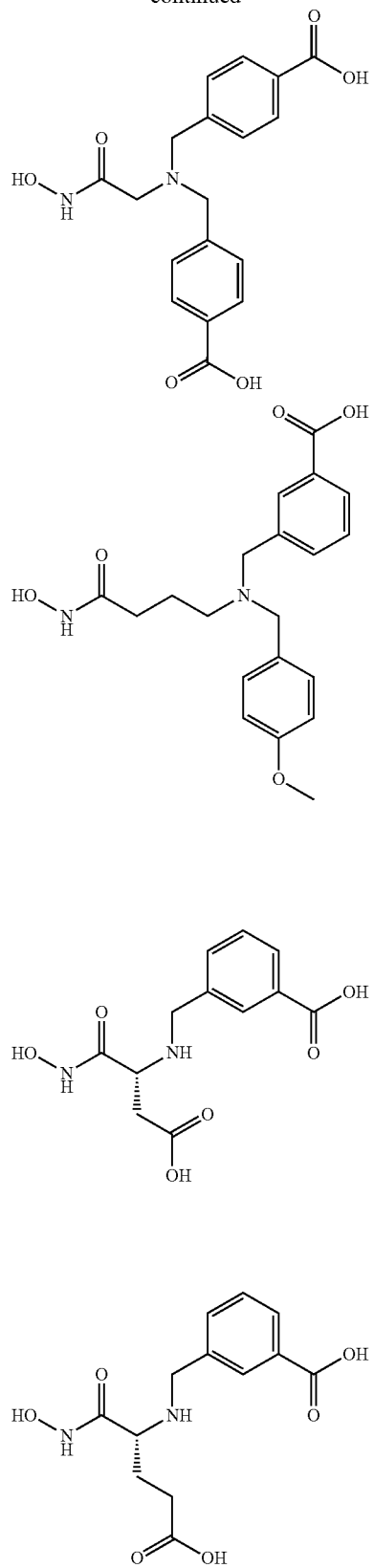

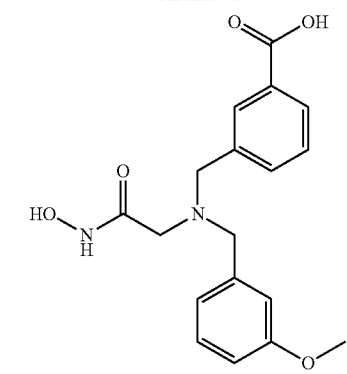
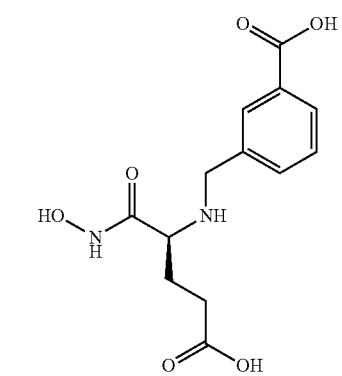
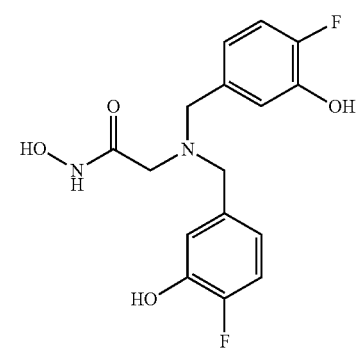
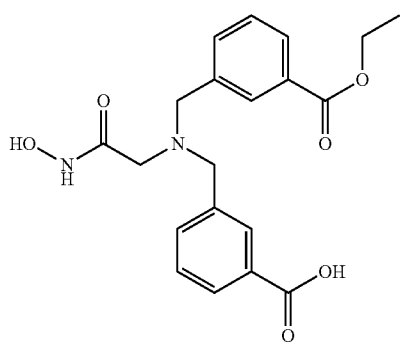
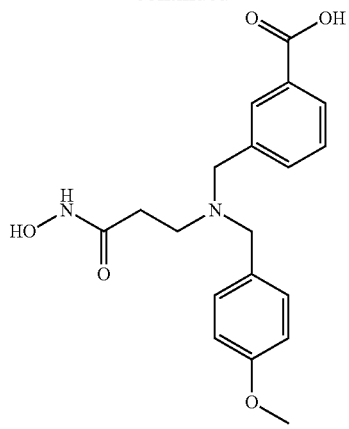
(ii) selected from the group consisting of:
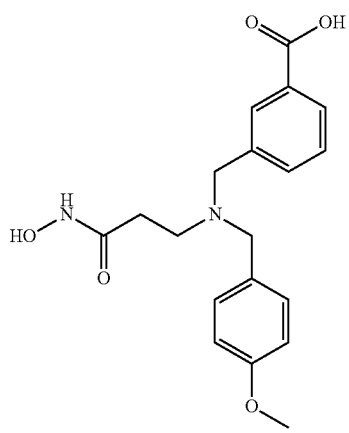
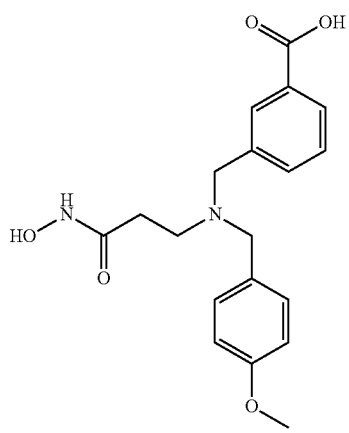

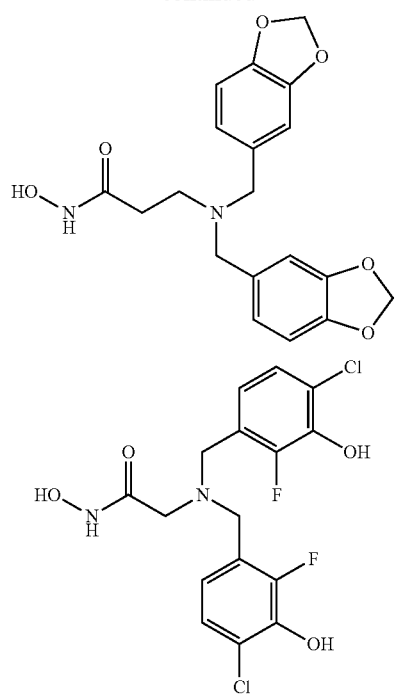
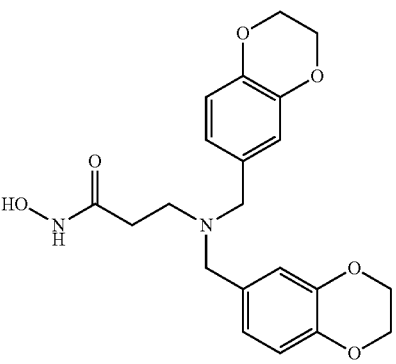
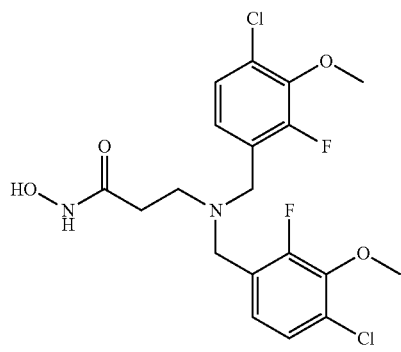
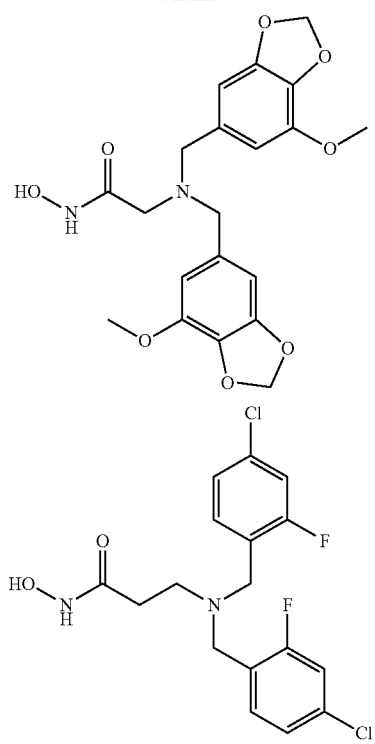
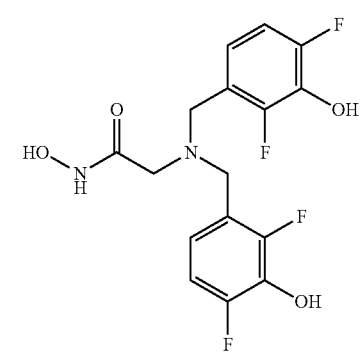
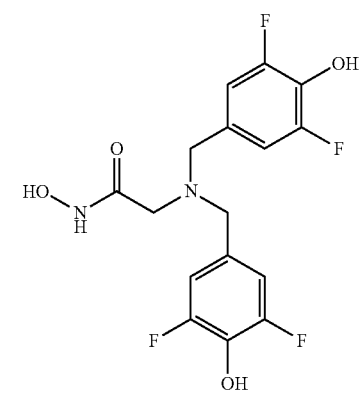

-continued

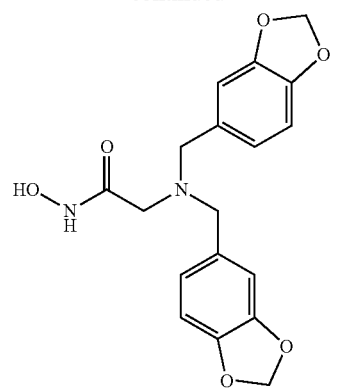

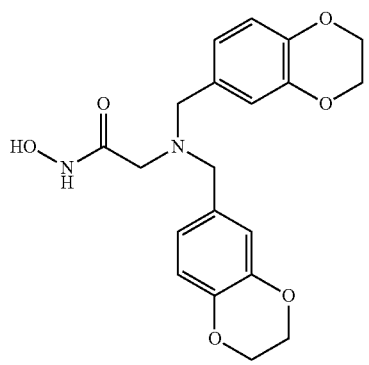

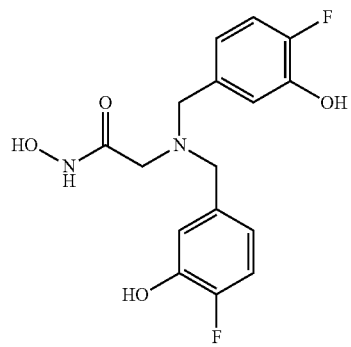

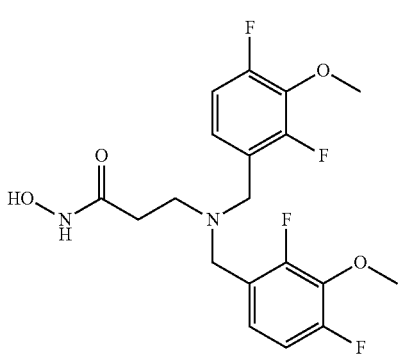

-continued

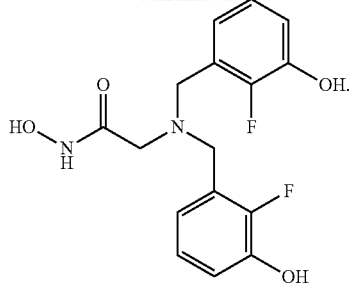

Pharmaceutical Compositions

Aspect 21 of the present invention provides a pharmaceutical composition comprising the compound according to any of the preceding aspects, its individual enantiomers, its individual diastereoisomers, its hydrates, its solvates, its crystal forms, its individual tautomers or a pharmaceutically acceptable salt thereof; and a pharmaceutically acceptable excipient as defined above.

Methods of Treatment and Compounds or Compositions for Use in Methods for Treatment or Prophylaxis The present invention provides a compound or a pharmaceutical composition according to any of the above aspects for use in a method for treatment or prophylaxis of the human or animal body by surgery or therapy.

The present invention also provides a method for treatment or prophylaxis of the human or animal body by surgery or therapy comprising administering a therapeutically effective amount of the compound or pharmaceutical composition according to any of the above aspects to a subject in need thereof.

The present invention also provides compound or a pharmaceutical composition according to any of the above aspects for use in a method for treatment or prophylaxis of Alzheimer's disease, nephritis, renal injury, renal ischemic injury, ischemic acute tubular necrosis, acute renal failure, bladder inflammation, inflammatory bowel disease (IBD), Crohn's disease, ulcerative colitis, chronic inflammation, colitis, fibrosis, fibrotic conditions, keloids, pulmonary hypertension, interstitial lung disease (ILD), or cancer, especially colorectal cancer.

The present invention also provides a method for treatment or prophylaxis of Alzheimer's disease, nephritis, renal injury, renal ischemic injury, ischemic acute tubular necrosis, acute renal failure, bladder inflammation, inflammatory bowel disease (IBD), Crohn's disease, ulcerative colitis, chronic inflammation, colitis, fibrosis, fibrotic conditions, keloids, pulmonary hypertension, interstitial lung disease (ILD), or cancer, especially colorectal cancer, comprising administering a therapeutically effective amount of the compound or pharmaceutical composition according to any of the above aspects to a subject in need thereof.

Methods for Producing the Compounds According to the Present Invention

The present invention also provides the following methods for producing the compounds according to Formulae I-V.

Scheme 1

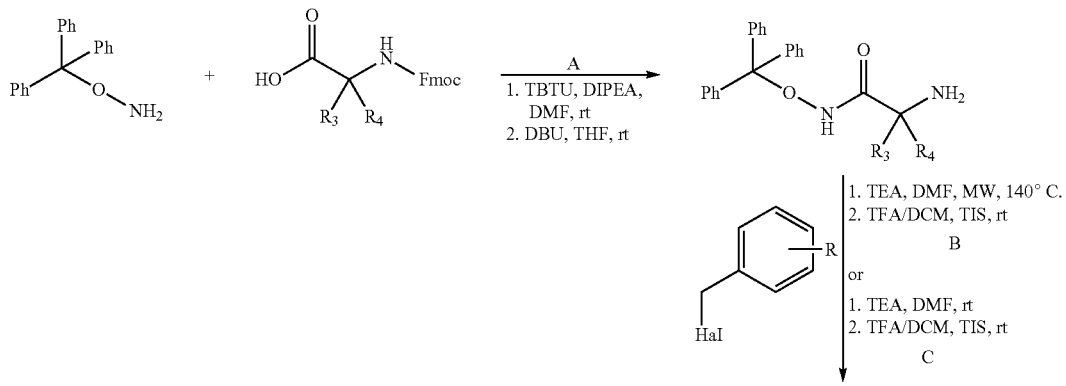

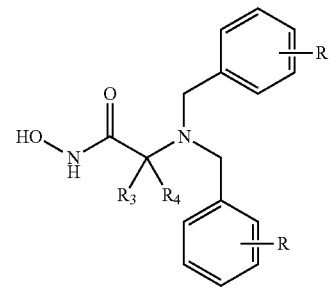

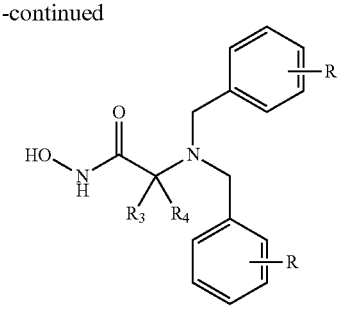

Method A:

Compounds of Formula I or V can be obtained by reacting the respective Fmoc-amino acid with tritylhydroxylamine in a suitable solvent, such as DMF, followed by addition of an activating agent, such as TBTU, and a base, such as DIPEA, followed by addition of water, collecting the resulting precipitate by filtration, optionally washing the precipitate with an organic solvent, such as an ether, and optionally with an aqueous base solution. The residue is then redissolved in a suitable organic solvent, such as THF, (and treated with a base, such as DBU, followed by optionally removing the solvent, and optionally purifying the residue.

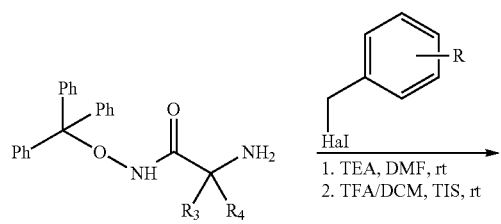

Method B/C:

Compounds of Formula I or V can be obtained by reacting at room temperature (Method B) or at elevated temperature (Method C), optionally under microwave irradiation at 140° C., the respective trityl protected hydroxamic acid with a base and the respective halide, preferably an optionally substituted benzyl halide, and optionally: extracting with an organic solvent, drying the combined organic phases removing the solvent, and purifying the residue; followed by treating the residue with triisopropylsilane and TFA; and optionally: extracting with an organic solvent, drying the combined organic phases, removing the solvent, and purifying the residue.

Scheme 2

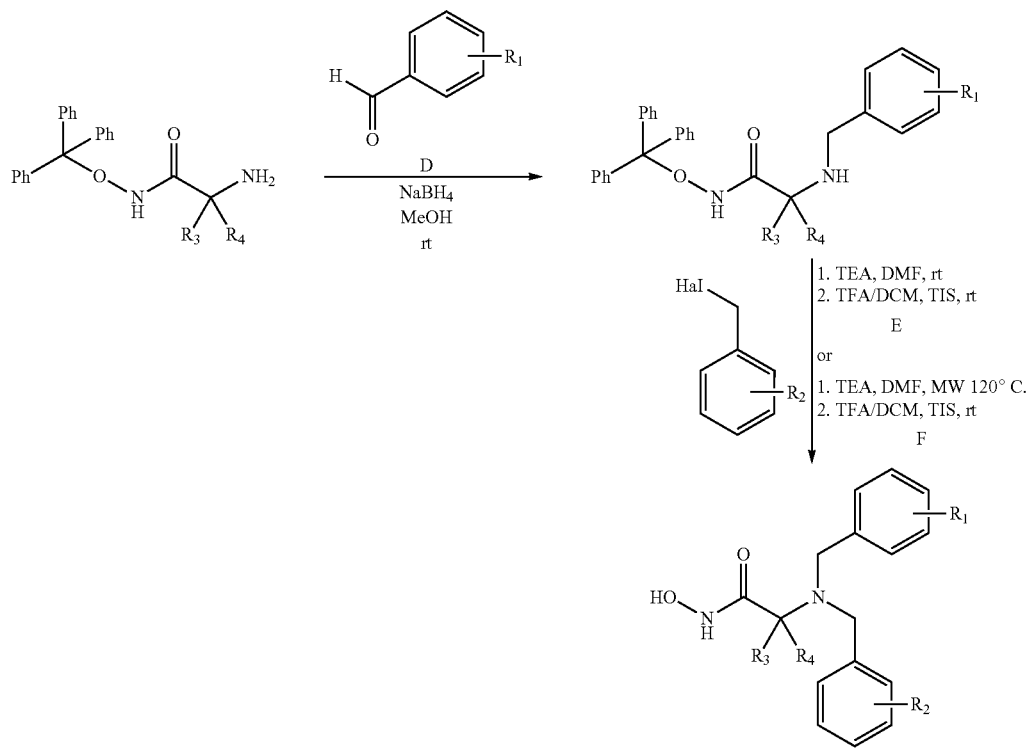

Methods D/E/F:

Compounds of Formula I or V can be obtained by reacting a suitable aldehyde (depending on $R^1$) with the trityl protected hydroxamic acid; then adding sodium borohydride; and optionally: extracting with an organic solvent, drying the combined organic phases removing the solvent, and purifying the residue, to obtain a trityl protected hydroxamic acid derivative (Method D); then reacting the trityl protected hydroxamic acid derivative with a base and the respective halide, preferably an optionally substituted benzyl halide, at room temperature (Method E) or at elevated temperature, optionally under microwave irradiation at 140° C. (Method F); and optionally: extracting with an organic solvent, drying the combined organic phases, removing the solvent, and purifying the residue; followed by treating the residue with triisopropylsilane and TFA; and optionally: extracting with an organic solvent, drying the combined organic phases, removing the solvent, and purifying the residue.

Scheme 3

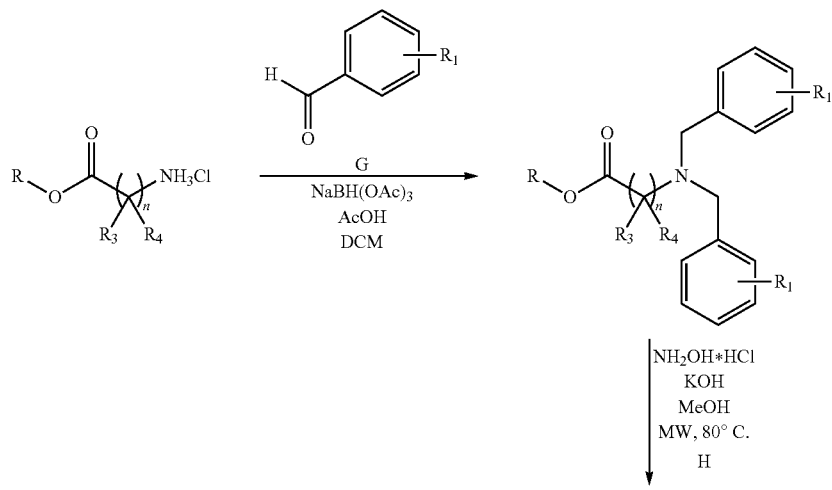

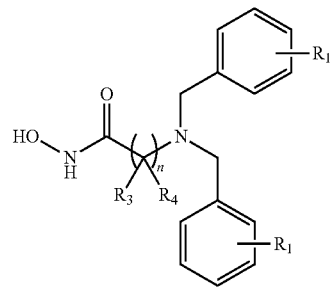

Methods G/H:

Compounds of Formula I or V can be obtained by reacting an amino acid ester and a respective aldehyde in a suitable solvent, treating with a reducing agent, such as sodium triacetoxy borohydride, and optionally a catalytic amount of acetic acid, followed by addition of water, extracting with an organic solvent, drying the combined organic phases removing the solvent, and purifying the residue (Method G). The respective amino acid ester derivative obtained by method G is dissolved a suitable solvent followed by addition of hydroxylamine hydrochloride and a base, such as sodium methanoxide, and preferably heating the mixture until completion, optionally under microwave irradiation at 80° C., followed by addition of water, extracting with an organic solvent, drying the combined organic phases removing the solvent, and purifying the residue.

Method A:

The respective Fmoc-amino acid (1 eq) was dissolved in DMF (1 ml/mmol). Tritylhydroxylamine (1 eq), TBTU (1 eq) and DIPEA (2 eq) were added and the mixture was stirred at room temperature for 1.5 h. The reaction was quenched with water. The resulting precipitate was collected by filtration and washed with diethyl ether and a small amount of saturated aqueous $NaHCO_3$. The residue was redissolved in THF (2 ml/mmol) and treated with DBU (1.5 eq). The mixture was stirred at room temperature until completion (TLC monitoring, usually about 30 min). The solvent was evaporated and the residue was purified by flash chromatography (silica, $CHCl_3$/MeOH gradient).

Method B:

The respective trityl protected hydroxamic acid (1 eq) obtained by method A was dissolved in DMF (5 ml/mmol). Triethylamine (2.2 eq) and the respective benzyl halide (2.2 eq) were added and the mixture was stirred at room temperature overnight. The reaction was quenched with water

Examples

Detailed Description of Synthetic Methods

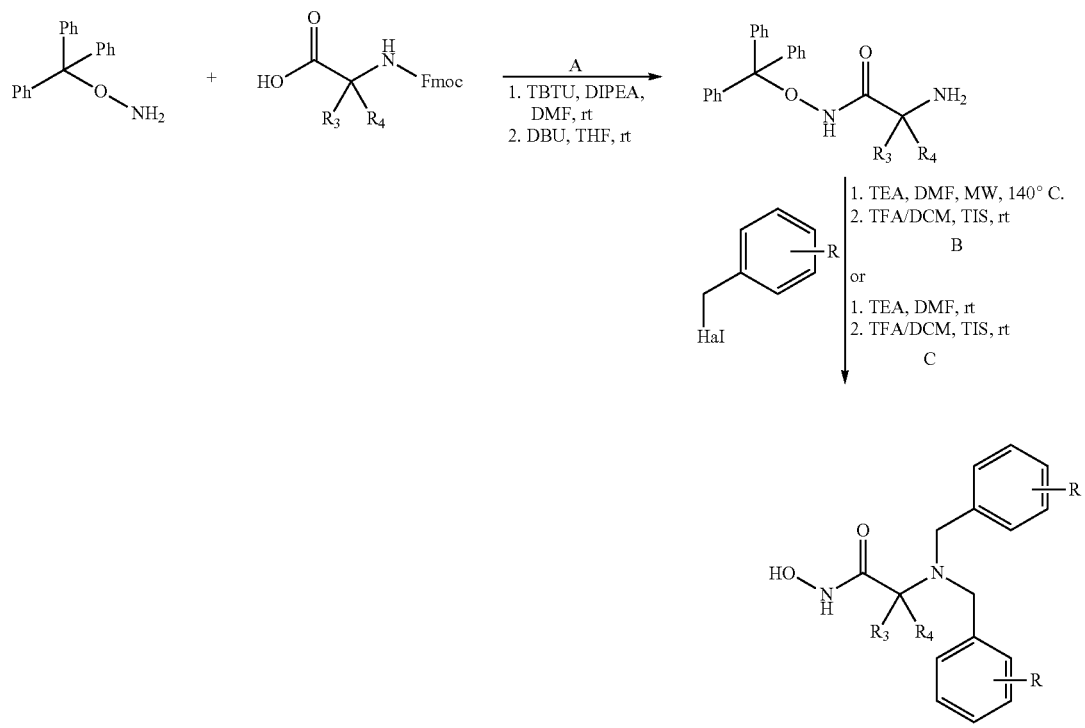

Scheme 1 and extracted with EtOAc (3×25 ml). The combined organic layers were dried over Na₂SO, and evaporated. The residue was treated with CH₂CH₂/TFA (1:1 v/v, 5 ml) and triisopropylsilane (1.5 eq) and stirred at room temperature for 2 hours. The volatiles were evaporated and the residue was purified by semi-preparative HPLC (Varian Prostar, Phenomenex Luna C₁₈ (2) column, H₂O/MeCN gradient containing 0.04% TFA).

Method C:

The respective trityl protected hydroxamic acid (1 eq) obtained by method A was dissolved in DMF (3-5 ml/mmol). Triethylamine (4 eq) and the respective benzyl halide (2.2 eq) were added and the mixture was heated in a microwave to 140° C. for 20 min. The reaction was quenched with water and extracted with EtOAc (3×25 ml). The combined organic layers were dried over Na₂SO₄ and evaporated. The residue was treated with CH₂Cl₂/TFA (1:1 v/v, 5 ml) and triisopropylsilane (1.5 eq) and stirred at room temperature for 2 hours. The volatiles were evaporated and the residue was purified by semi-preparative HPLC (Varian 20 mmol, 2 eq) and DBU (2.2 ml, 15 mmol, 1.5 eq) according to method A. Yield: 1.4 g (42.1%), ESI-MS: m/z 243.2 [Trityl]⁺, 333. 3 [M+H]⁺; HPLC (gradient 2): rt 12.24 min (100%).

Step 2:3-{[(3-Carboxyphenyl)methyl-[2-(hydroxyamino)-2-oxo-ethyl]amino]methyl]benzoic acid The compound was synthesized starting from 2-Amino-N-trityloxy-acetamide (332 mg, 1 mmol, 1 eq), tert-butyl 3-(chloromethyl)benzoate (499 mg, 2.2 mmol, 2.2 eq) and TEA (305 µl, 2.2 mmol, 2.2 eq) followed by acidic deprotection and purification by semi-preparative HPLC as described in method B. Yield: 43 (12%, TFA salt); ESI-MS: m/z 359.1 [M+H]⁺; HPLC (gradient 2): rt 7.73 min (97.4%); ¹H-NMR, 400 MHZ, DMSO d6: δ3.59 (s, 1.5H), 3.91 (s, 0.5H), 4.24-4.28 (m, 2H), 7.55-7.59 (m, 1H), 7.70-7.74 (m, 1H), 7.95-7.99 (m, 1H), 8.13-8.15 (m, 1H), 9.21-9.58 (m, 3H), 10.69 (s, 0.2H), 10.94 (s, 0.8H), 13.19 (br s, 1H).

Scheme 2

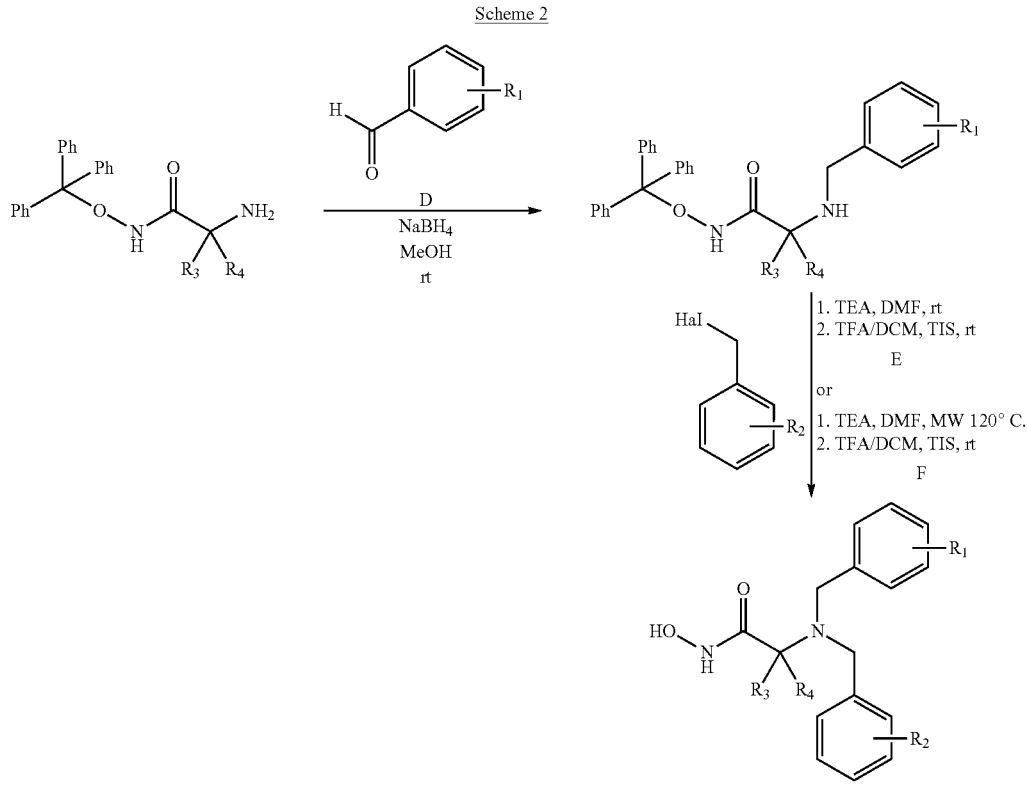

Prostar, Phenomenex Luna C₁₈ (2) column, H₂O/MeCN gradient containing 0.04% TFA).

Synthesis Example 2

3-[[(3-Carboxyphenyl)methyl-[2-(hydroxyamino)-2-oxo-ethyl]amino]methyl]benzoic acid Step 1:2-Amino-N-trityloxy-acetamide The compound was synthesized starting from Fmoc-Gly-OH (2.97 g, 10 mmol, 1 eq), Tritylhydroxylamine (2.8 g, 10 mmol, 1 eq), TBTU (3.21 g, 10 mmol, 1 eq), DIPEA (3.5 ml, Method D:

The respective trityl protected hydroxamic acid (1 eq) obtained by method A was dissolved in MeOH (10 ml/mmol). Tert-butyl 3-formylbenzoate (1.1 eq), or another suitable aldehyde, was added and the mixture was stirred at room temperature. After 3 h sodium borohydride (1.2 eq) was added carefully in small portions. The reaction was stirred at the same temperature for further 30 min. The mixture was quenched with water and extracted with EtOAc (3×25 ml). The solvent was evaporated and the residue was purified by flash chromatography (silica, CHCl₃/MeOH gradient).

Method E:

The trityl protected hydroxamic acid derivative (1 eq) obtained by method D was dissolved in DMF (5 ml/mmol). Triethylamine (1.1 eq) and the respective benzyl halide (1.1 eq) were added and the mixture was stirred at room temperature overnight. The reaction was diluted with water and extracted with EtOAc (3×25 ml). The combined organic layers were dried over Na$_2$SO$_4$ and evaporated. The residue was with CH$_2$Cl$_2$/TFA (1:1 5 and treated v/V, ml)triisopropysilane (1.5 eq). After stirring at room temperature for 2 hours, the volatiles were evaporated. The residue was purified by semi-preparative HPLC (Varian Prostar, Phenomenex Luna C$_{18}$ (2) column, H$_2$O/MeCN gradient containing 0.04% TFA) or by flash chromatography (silica, CHCl$_3$/MeOH gradient).

Method F:

The trityl protected hydroxamic acid derivative (1 eq) obtained by method D was dissolved in DMF (5 ml/mmol).

Synthesis Example 7

3-[[(4-Carboxyphenyl)methyl-[2-(hydroxyamino)-2-oxo-ethyl]amino]methyl]benzoic acid The compound was synthesized starting from tert-Butyl 3-[[[2-oxo-2-(trityloxyamino)ethyl]amino]-methyl]benzoate (method D-see above, 410 mg, 0.78 mmol, 1 eq), 4-Bromomethylbenzoic acid tert butyl ester (234 mg, 0.86 mmol, 1.1 eq) and TEA (120 µl, 0.86 mmol, 1.1 eq) and purified by semi-preparative HPLC according to method E. Yield: 35 mg (12.5%, TEA-salt); ESI-MS: m/z 359.1 [M+H]$^+$; HPLC (gradient 1): rt 7.01 min (100%); $^1$H-NMR, 400 MHZ, DMSO d6: δ 3.18 (m, 2H), 4.00 (m, 4H), 7.49-7.63 (m, 3H), 7.69-7.75 (m, 1H), 7.89-7.99 (m, 3H), 8.02-8.14 (m, 1H), 9.35-9.37 (m, 1H), 10.60 (br s, 1H), 13.04 (br s, 2H).

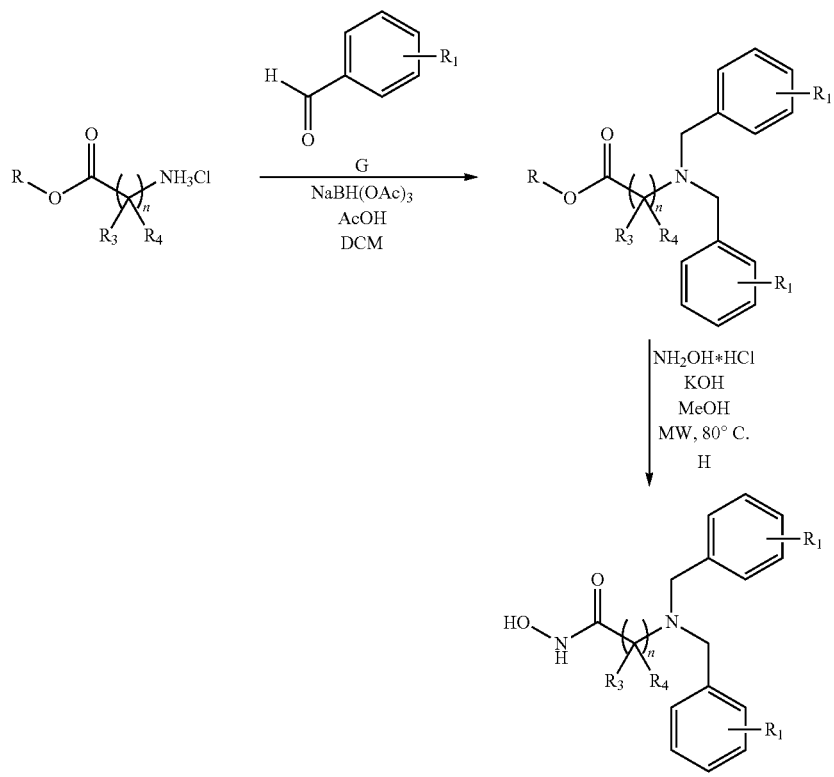

Scheme 3

Triethylamine (1.1 eq) and the respective benzyl halide (1.1 eq) were added and the mixture was heated to 120° C. under microwave irradiation for 15 min. After cooling to room temperature, the reaction was diluted with water and extracted with EtOAc (3×25 ml). The combined organic layers were dried over Na$_2$SO$_4$ and evaporated. The residue was treated with CH$_2$Cl$_2$/TFA (1:1 v/v, 5 ml) and triisopropysilane (1.5 eq). After stirring at room temperature for 2 hours, the volatiles were evaporated. The residue was purified by semi-preparative HPLC (Varian Prostar, Phenomenex Luna C$_{18}$ (2) column, H$_2$O/MeCN gradient containing 0.04% TFA) or by flash chromatography (silica, CHCl$_3$/MeOH gradient).

Method G:

The amino acid ester (1 eq) and the respective aldehyde (3 eq) were suspended in dichloromethane (20 ml/mmol) and treated with sodium triacetoxy borohydride (4 eq) and a catalytic amount of acetic acid. was stirred room The mixture at temperature overnight. The reaction was quenched by addition of water and extracted with EtOAc (3×25 ml). The combined organic layers were dried over Na$_2$SO$_4$ and evaporated. The residue was purified by flash chromatography (silica, heptane/diethyl ether gradient).

Method H:

The respective amino acid ester derivative (1 eq) obtained by method G was in MeOH dissolved (6-10 ml). Hydroxylamine hydrochloride (3 eq) and sodium methanoxide (6 eq) were added and the mixture was heated in a microwave (Biotage® initiator+) at 80° C. upon completion (usually 6-10 min). After cooling to room temperature the mixture water. was diluted with The pH was adjusted to ≈8 by means of diluted aqueous HCl and the mixture was extracted with EtOAc (3×25 ml). The combined organic layers were dried over $Na_2SO_4$ and evaporated. The residue was purified by semi-preparative HPLC (Varian Prostar, Phenomenex Luna $C_{18}$ (2) column, $H_2O$/MeCN gradient containing 0.04% TFA).

Synthesis Example 63

2-[bis(2, 3-Dihydro-1, 4-benzodioxin-6-ylmethyl) amino]ethanehydroxamic acid (660)

Step 1: Methyl 2-[bis(2, 3-dihydro-1, 4-benzodioxin-6-ylmethyl)amino]acetate

The compound was synthesized starting from glycine methylester hydrochloride (126 mg, 1 mmol, 1 eq), 1, 4-Benzodioxane-6-carbaldehyde (492 mg, 3 mmol, 3 eq) and sodium triacetoxy borohydride (848 mg, 4 mmol 4 eq) according to method G. Yield: 322 mg (83,5%), ESI-MS: m/z 386.9 [M+H]$^+$; HPLC (gradient 2): rt 11.09 min (97.2%)

Step 2:2-[bis(2, 3-Dihydro-1, 4-benzodioxin-6-ylmethyl)amino]ethanehydroxamic acid The compound was synthesized starting from Methyl 2-[bis(2, 3-dihydro-1, 4-benzodioxin-6-ylmethyl)amino]acetate (322 mg, 0.84 mmol, 1 eq), $NH_2OH*HCl$ (175 mg, 2.5 mmol, 3 eq) and sodium methoxide (0.9 ml 30% in MeOH, 5 mmol, 6 eq) according to method H. Yield: 35 mg (10.9%, TFA-salt); ESI-MS: m/z 387.1 [M+H]$^+$; HPLC (gradient 2): rt 9.75 min (97.7%); $^1$H-NMR, 400 MHZ, DMSO d6: δ 3.41 (br s, 2H), 4.12 (br s, 4H), 4.26 (s, 8H), 6.89-6.99 (m, 4H), 7.04-7.09 (m, 2H), 10.88 (br s, 1H).

Further Examples

Series 4

Example 1:4-[[(4-Carboxyphenyl)methyl-[2-(hydroxyamino)-2-oxo-ethyl]amino]methyl]benzoic acid The compound was synthesized using method B as described above. Yield: 12 mg (3.3%,); ESI-MS: m/z 359.3 [M+H]$^+$; HPLC (gradient 2): rt 7.39 min (100%); $^1$H-NMR, 400 MHZ, DMSO d6: δ 3.10 (s, 2H), 3.90 (s, 4H), 7.54-7.56 (m, 4H), 7.91-7.93 (m, 4H), 10.52 (br s, 1H), 12.94 (br s, 2H).

Example 2:3-[[(3-Carboxyphenyl)methyl-[2-(hydroxyamino)-2-oxo-ethyl]amino]methyl]benzoic acid The compound was synthesized using method A & B as described above. Yield: 43 mg (12.0%,); ESI-MS: m/z 359.1 [M+H]$^+$; HPLC (gradient 2): rt 7.73 min (97.4%); $^1$H-NMR, 400 MHZ, DMSO d6: δ 3.24 (br s, 1H), 4.07 (br s, 3.1 H), 4.43 (br s, 0.9 H), 7.49-7.58 (m, 2H), 7.68-7.74 (m, 2H), 7.89-7.97 (m, 2H), 8.03 (br s, 1.6H), 8.14 (br s, 0.4H), 10.64 (s, 1H), 13.06 (br s, 2H).

Example 3:3-[[[2-(Hydroxyamino)-2-oxo-ethyl] amino]-methyl]benzoic acid

Side product of Example 2. Yield: 24 mg (10.7%); ESI-MS: m/z 224.9 [M+H]$^+$; HPLC (gradient 2): rt 3.84 min (99.1%); $^1$H-NMR, 400 MHz, DMSO d6: δ 3.59 (s, 1.5H), 3.91 (s, 0.5H), 4.24-4.28 (m, 2H), 7.55-7.59 (m, 1H), 7.70-7.74 (m, 1H), 7.95-7.99 (m, 1H), 8.13-8.15 (m, 1H), 9.21-9.58 (m, 3H), 10.69 (s, 0.2H), 10.94 (s, 0.8H), 13.19 (br s, 1H).

Example 4:2-[bis(1, 3-Benzodioxol-5-ylmethyl) amino]-ethanehydroxamic acid

The compound was synthesized using method B as described above. Yield: 56 mg (11.9%,); ESI-MS: m/z 359.1 [M+H]$^+$; HPLC (gradient 2): rt 10.03 min (100%); $^1$H-NMR, 400 MHZ, DMSO d6: δ 3.40 (s, 2H), 4.12 (br s, 3H), 4.33 (br s, 1H), 6.06-6.07 (m, 4H), 6.96-7.03 (m, 4H), 7.09-7.13 (m, 2H), 9.51 (br s, 1H), 10.67-10.85 (m, 1H).

Example 5:2-[bis[(3-Methoxyphenyl)methyl] amino]-ethanehydroxamic acid

The compound was synthesized using method B as described above. Yield: 102 mg (23.0%,); ESI-MS: m/z 331.1 [M+H]+; HPLC (gradient 2): rt 10.85 min (100%); $^1$H-NMR, 400 MHZ, DMSO d6: δ 3.35 (br s, 2H), 3.77 (s, 6H), 4.10 (br s, 3H), 4.38 (br s, 1H), 6.94-7.13 (m, 6H), 7.31-7.38 (m, 2H), 10.78 (br s, 1H).

Example 6:3-[[[2-(Hydroxyamino)-2-oxo-ethyl]-[(4-methoxyphenyl)methyl]amino]-methyl]benzoic acid The compound was synthesized using methods D & E as described above. Yield: 84 mg (36.7%,); ESI-MS: m/z 345.5 [M+H]$^+$; HPLC (gradient 2): rt 8.72 min (98.2%); $^1$H-NMR, 400 MHZ, DMSO d6: δ 3.30-3.43 (m, 2H), 3.78 (s, 3H), 4.07-4.49 (m, 4H), 6.96-7.01 (m, 2H), 7.39-7.47 (m, 1H), 7.52-7.59 (m, 2H), 7.71-7.78 (m, 1H), 7.94-8.00 (m, 1H), 8.09-8.19 (m, 1H), 9.02-9.43 (m, 1H), 10.62-10.75 (m, 1H), 13.12 (br s, 1H).

Example 7:3-[[(4-Carboxyphenyl)methyl-[2-(hydroxyamino)-2-oxo-ethyl]amino]methyl]benzoic acid The compound was synthesized using methods D & E as described above. Yield: 35 mg (12.5%,); ESI-MS: m/z 359.1 [M+H]$^+$; HPLC (gradient 1): rt 7.01 min (100%); $^1$H-NMR, 400 MHZ, DMSO d6: δ 3.18 (m, 2H), 4.00 (m, 4H), 7.49-7.63 (m, 3H), 7.69-7.75 (m, 1H), 7.89-7.99 (m, 3H), 8.02-8.14 (m, 1H), 9.35-9.37 (m, 1H), 10.60 (br s, 1H), 13.04 (br s, 2H).

Example 8:3-[[[2-(Hydroxyamino)-2-oxo-ethyl]-[(4-biphenyl)methyl]amino]-methyl]benzoic acid The compound was synthesized using methods D & E as described above. Yield: 60 mg (40.3%,); ESI-MS: m/z 391.9 [M+H]$^+$; HPLC (gradient 1): rt 11.57 min (100%); $^1$H-NMR, 400 MHZ, DMSO 3.89-4.50 (m, 6H), 7.39-7.42 (m, 1H), 7.46-7.63 (m, 5H), 7.68-7.79 (m, 5H), 7.92-7.99 (m, 1H), 8.09-8.20 (m, 1H), 9.33 (br s, 1H), 10.71 (s, 1H), 13.05 (br s, 1H).

Example 9: 3-[[[2-(Hydroxyamino)-2-oxo-ethyl]-[(4-propoxyphenyl)methyl]amino]-methyl]benzoic acid The compound was synthesized using methods D & F as described above. Yield: 110 mg (55.3%,); ESI-MS: m/z 373.4 [M+H]$^+$; HPLC (gradient 1): rt 10.29 min (97.34%); $^1$H-NMR, 400 MHZ, DMSO d6: δ 0.98 (t, 3H, 3J=7.5 Hz), 1.73 (q, 2H, 3J=7.5 Hz), 3.84-4.45 (m, 8H), 6.94-6.99 (m, 2H), 7.36-7.45 (m, 2H), 7.52-7.59 (m, 1H), 7.71-7.76 (m, 1H), 7.93-8.00 (m, 1H), 8.08-8.19 (m, 1H), 9.08 (br S, 1H), 10.74 (s, 1H), 13.10 (br s, 1H).

Example 10: 3-[[(3-Fluoro-4-methoxy-phenyl)methyl-[2-(hydroxyamino)-2-oxo-ethyl]amino]methyl]benzoic acid The compound was synthesized using methods D & F as described above. Yield: 95 mg (34.3%,); ESI-MS: m/z 363.1 [M+H]$^+$; HPLC (gradient 1): rt 8.40 min (97.78%); $^1$H-NMR, 400 MHZ, DMSO d6:0 3.84-4.06 (m, 9H), 7.14-7.40 (m, 3H), 7.50-7.58 (m, 1H), 7.69-7.75 (m, 1H), 7.90-8.14 (m, 2H), 10.68 (s, 1H), 13.06 (br s, 1H).

Example 11: 3-[[(2, 6-Difluoro-4-methoxy-phenyl)methyl-[2-(hydroxyamino)-2-oxo-ethyl]amino]methyl]benzoic acid The compound was synthesized using methods D & F as described above. Yield: 40 mg (17.0%); ESI-MS: m/z 380.9 [M+H]$^+$; HPLC (gradient 1): rt 9.36 min (97.7%); $^1$H-NMR, 400 MHZ, DMSO d6: δ 3.77-3.83 (m, 5H), 3.92-3.93 (m, 4H), 6.72-6.84 (m, 2H), 7.44-7.48 (m, 1H), 7.62-7.64 (m, 1H), 7.84-7.87 (m, 1H), 7.95-7.97 (m, 1H), 10,47 (s, 1H), 13,00 (br s, 1H).

Example 12: 3-[[(2R)-2-(Hydroxycarbamoyl) pyrrolidin-1-yl]methyl]benzoic acid The compound was synthesized using method A & F as described above. Yield: 31 mg (25.0%,); ESI-MS: m/z 265.3 [M+H]$^+$; HPLC (gradient 2): rt 3.76 min (99.9%); $^1$H-NMR, 400 MHZ, DMSO d6: δ 1.82-1.90 (m, 2H), 2.02-2.14 (m, 1H), 2.33-2.43 (m, 1H), 3.48-3.54 (m, 2H), 3.93-4.02 (m, 1H), 4.36-4.60 (m, 2H), 7.57 (t, 1H, 3J=7.5 Hz), 7.71-7.75 (m, 1H), 8.00 (d, 1H, 3J=7.9 Hz), 8.12-8.15 (m, 1H), 9.29 (br s, 1H), 11.08 (br s, 1H), 13.19 (br s, 1H).

Example 13: 3-[[(2S)-2-(Hydroxycarbamoyl) pyrrolidin-1-yl]methyl]benzoic acid The compound was synthesized using methods A & F as described above. Yield: 67 ESI-MS: m/z 265.2 mg (42.2%,); [M+H]$^+$; HPLC (gradient 2): rt 3.71 min (100%); $^1$H-NMR, 400 MHZ, DMSO d6: δ 1.84-1.91 (m, 2H), 2.05-2.12 (m, 1H), 2.34-2.41 (m, 1H), 3.25-3.34 (m, 2H), 3.97-4.02 (m, 1H), 4.35-4.60 (m, 2H), 7.57 (t, 1H, 3J=7.5 Hz), 7.71-7.75 (m, 1H), 8.00 (d, 1H, 3J=7.5 Hz), 8.12-8.15 (m, 1H), 9.30 (br s, 1H), 11.09 (s, 1H), 13.18 (br s, 1H).

Example 14: 3-[[[2-(Hydroxyamino)-2-oxo-ethyl]-[(3-methoxyphenyl)methyl]amino]-methyl]benzoic acid The compound was synthesized using methods D & F as described above. Yield: 150 mg (36.7%,); ESI-MS: m/z 345.1 [M+H][+; HPLC (gradient 1): rt 8.21 min (98.6%); $^1$H-NMR, 400 MHZ, DMSO d6: δ 3.27 (s, 2H), 3.76-4.47 (m, 7H), 6,90-6.93 (m, 1H), 7.00-7.11 (m, 2H), 7.28-7.37 (m, 1H), 7.50-7.58 (m, 1H), 7.69-7.76 (m, 1H), 7.91-7.98 (m, 1H), 8.07-8.17 (m, 1H), 10,68 (s, 1H), 13.07 (br s, 1H).

Example 15: 2-[bis[(4-Methoxyphenyl)methyl]amino]ethane-hydroxamic acid

The compound was synthesized using methods B as described above. Yield: 40 mg (7.7%,); ESI-MS: m/z 331.4 [M+H]$^+$; HPLC (gradient 1): rt 9.63 min (89.7%); $^1$H-NMR, 400 MHZ, DMSO d6: δ 3.75-3.80 (m, 6H), 3.98-4.45 (m, 6H), 6.93-7.16 (m, 6H), 7.30-7.40 (m, 2H), 10.75 (br s, 1H).

Example 16: 2-[[[2-(Hydroxyamino)-2-oxo-ethyl]-[(4-methoxyphenyl)methyl]amino]-methyl]benzoic acid The compound was synthesized using methods D & F as described mg above. Yield: 23 (6.7%,); ESI-MS: m/z 345.3 [M+H]$^+$; HPLC (gradient 2): rt 9.31 min (100%); $^1$H-NMR, 400 MHZ, DMSO d6: δ 3.46-3.52 (m, 2H), 3.78-3.79 (m, 3H), 4.22-4.35 (m, 2H), 4.54-4.70 (m, 2H), 6.97-7.03 (m, 2H), 7.39-7.49 (m, 2H), 7.53-7.70 (m, 3H), 7.95-8.02 (m, 1H), 9.20-9.51 (m, 1H), 10.58-10.78 (m, 1H).

Example 17: 3-[[Benzyl-[2-(hydroxyamino)-2-oxo-ethyl]-aminomethyl]benzoic acid The compound was synthesized using methods D & F as described above. Yield: 160 mg (76.4%,); ESI-MS: m/z 315.0 [M+H]$^+$; HPLC (gradient 1): rt 7.63 min (100%); $^1$H-NMR, 400 MHZ. DMSO d6:4. 01-4.39 (m, 6H), 7.34-7.76 (m, 7H), 7.91-8.18 (m, 2H), 8.98 (br S, 1H), 10.65 (s, 1H), 13.08 (br s, 1H).

Example 18: 3-[[[2-(Hydroxyamino)-2-oxo-ethyl]-(p-tolyl-methyl)amino]methyl]benzoic acid The compound was synthesized using methods D & F as described above. Yield: 150 mg (68.6%,); ESI-MS: m/z 329.1 [M+H]$^+$; HPLC (gradient 1): rt 8.72 min (100%); $^1$H-NMR, 400 MHZ, DMSO d6: δ 2.31 (s, 3H), 3.70-4.44 (m, 6H), 7.18-7.40 (m, 4H), 7.49-7.57 (m, 1H), 7.69-7.76 (m, 1H), 7.89-8.15 (m, 2H), 8.98 (br s, 1H), 10,61 (s, 1H), 13.05 (br s, 1H).

Example 19: 3-[[(4-Cyanophenyl)methyl-[2-(hydroxyamino)-2-oxo-ethyl]amino]methyl]benzoic acid The compound was synthesized using methods D & F as described above. Yield: 200 mg (88.5%,); ESI-MS: m/z 340.1 [M+H]$^+$; HPLC (gradient 1): rt 8.88 min (100%); $^1$H-NMR, 400 MHZ, DMSO d6: δ 3.10 (s, 2H), 3.88-3.92 (m, 4H), 7.44-7.53 (m, 1H), 7.61-7.71 (m, 3H), 7.81-8.06 (m, 4H), 10.54 (s, 1H), 12.98 (br s, 1H).

Example 20: 3-[[(4-Chlorophenyl)methyl-[2-(hydroxyamino)-2-oxo-ethyl]amino]methyl]benzoic acid The compound was synthesized using methods D & F as described above. Yield: 170 mg (71.0%,); ESI-MS: m/z 349.2 [M+H]$^+$; HPLC (gradient 1): rt 9.55 min (97.0%); $^1$H-NMR, 400 MHZ, DMSO d6: δ 3.18 (s, 2H), 3.93-3.99

(m, 4H), 7.35-7.60 (m, 5H), 7.64-7.74 (m, 1H), 7.87-8.14 (m, 2H), 10.61 (s, 1H), 13.03 (br s, 1H).

Example 21:3-[[(4-Fluorophenyl)methyl-[2-(hydroxyamino)-2-oxo-ethyl]amino]methyl]benzoic acid The compound was synthesized using methods D & F as described above. Yield: 150 mg (59.0%,); ESI-MS: m/z 333.2 [M+H]$^+$; HPLC (gradient 1): rt 8.21 min (100%); $^1$H-NMR, 400 MHZ, DMSO d6: δ 3.98-4.04 (m, 4H), 4.34-4.40 (m, 2H), 7.19-7.28 (m, 2H), 7.47-7.57 (m, 3H), 7.69-7.75 (m, 1H), 7.90-8.15 (m, 2H), 8.99 (br s, 1H), 10.65 (s, 1H), 13.05 (br s, 1H).

Example 22:3-[[1, 3-Benzodioxol-5-ylmethyl-[2-(hydroxy-amino)-2-oxo-ethyl]amino]-methyl]benzoic acid The compound was synthesized using methods D & F as described above. Yield: 210 mg (76.6%,); ESI-MS: m/z 359.2 [M+H]$^+$; HPLC (gradient 1): rt 7.95 min (100%); $^1$H-NMR, 400 MHZ, DMSO d6:3. 85-4.43 (m, 6H), 6.02-6.06 (m, 2H), 6.89-7.00 (m, 2H), 7.06-7.10 (m, 1H), 7.51-7.58 (m, 1H), 7.70-7.76 (m, 1H), 7.91-7.99 (m, 1H), 8.05-8.16 (m, 1H), 9.07 (br s, 1H), 10.70 (s, 1H), 13.07 (m, 1H).

Example 23:2-[1, 3-Benzodioxol-5-ylmethyl-[(4-ethoxy-phenyl)methyl]amino]ethanehydroxamic acid The compound was synthesized using methods D & F as described above. Yield: 195 mg (58.9%,); ESI-MS: m/z 121.1 [M-C$_{10}$H$_{11}$N$_2$O$_4$]$^+$; 345.3 [M+H]$^+$; HPLC (gradient 1): rt 9.07 min (100%); $^1$H-NMR, 400 MHz, DMSO d6: δ 3.35-3.45 (m, 2H), 3.74-3.80 (m, 3H), 4.06-4.40 (m, 4H), 6.06-6.08 (m, 2H), 6.96-7.04 (m, 4H), 7.10-7.14 (m, 1H), 7.42-7.49 (m, 2H), 9.12 (br s, 1H), 10.84 (br s, 1H).

Example 24:2-[(4-Methoxyphenyl)methyl-(p-tolyl-methyl)-amino]ethanehydroxamic acid The compound was synthesized using methods D & F as described above. Yield: 170 mg (56.3%,); ESI-MS: m/z 121.1 [M-C$_{10}$H$_{13}$N$_2$O$_2$]$^+$; 315.3 [M+H]$^+$; HPLC (gradient 1): rt 9.92 min (100%); $^1$H-NMR, 400 MHz, DMSO d6: δ 2.33 (s, 3H), 3.33-3.40 (m, 2H), 3.71-3.83 (m, 3H), 4.05-4.45 (m, 4H), 6.98-7.02 (m, 2H), 7.24-7.28 (m, 2H), 7.38-7.49 (m, 4H), 9,16 (br s, 1H), 10.82 (br s, 1H).

Example 25:2-[(4-fluorophenyl)methyl-[(4-methoxyphenyl)-methyl]amino]ethanehydroxamic acid The compound was synthesized using methods D & F as described above. Yield: 210 mg (68.6%,); ESI-MS: m/z 121.1 [M–C$_9$H$_{10}$FN$_2$O$_2$]$^+$; 341.3 [M+Na]$^+$; HPLC (gradient 1): rt 9.15 min (100%); $^1$H-NMR, 400 MHZ, DMSO d6: δ 3.26-3.47 (m, 2H), 3.73-3.79 (m, 3H), 4.01-4.38 (m, 4H), 6.97-7.02 (m, 2H), 7.23-7.31 (m, 2H), 7.40-7.62 (m, 4H), 9.05 (br s, 1H), 10.77 (br s, 1H).

Example 26:2-[(4-Chlorophenyl)methyl-[(4-methoxyphenyl)-methyl]amino]ethanehydroxamic acid The compound was synthesized using methods D & F as described above. Yield: 153 mg (47.5%,); ESI-MS: m/z 121.1 [M–C$_9$H$_{10}$ClN$_2$O$_2$]$^+$; 357.3 [M+Na]$^+$; HPLC (gradient 1): rt 10.29 min (100%); $^1$H-NMR, 400 MHz, DMSO d6: δ 3.24-3.40 (m, 2H), 3.75-3.81 (m, 3H), 3.98-4.43 (m, 4H), 6.96-7.01 (m, 2H), 7.39-7.62 (m, 6H), 9.10 (br S, 1H), 10.74 (br s, 1H).

Example 27:2-[(3-Methoxyphenyl)methyl-[(4-methoxyphenyl)-methyl]amino]ethanehydroxamic acid The compound was synthesized using methods D & F as described above. Yield: 165 mg (52.0%,); ESI-MS: m/z 121.1 [M–C$_{10}$H$_{13}$N$_2$O$_3$]$^+$; 353.3 [M+Na]$^+$; HPLC (gradient 1): rt 14.59 min (100%); $^1$H-NMR, 400 MHZ, DMSO d6: δ 3.32-3.46 (m, 2H), 3.75-3.81 (m, 6H), 4.05-4.44 (m, 4H), 6.98-7.15 (m, 5H), 7.33-7.49 (m, 3H), 9.15 (br s, 1H), 10.82 (br s, 1H).

Example 28:3-[[[(1S)-2-(Hydroxyamino)-1-methyl-2-oxo-ethyl]amino]methyl]benzoic acid The compound was synthesized using methods A & D as described above followed by deprotection with TFA/DCM (1:1 v/v). Yield: 52 mg (20.9%,); ESI-MS: m/z 239.0 [M+H]$^+$; HPLC (gradient 1): rt 3.52 min (100%); $^1$H-NMR, 400 MHZ, DMSO d6: δ 1.36-1.51 (m, 3H), 3.67-3.78 (m, 1H), 4.06-4.26 (m, 2H), 7.54-7.62 (m, 1H), 7.67-7.75 (m, 1H), 7.96-8.03 (m, 1H), 8.11-8. 18 (m, 1H), 9.14-9.59 (m, 3H), 11.14 (s, 1H), 13.21 (br s, 1H).

Example 29:3-[[[(1S)-1-(Hydroxycarbamoyl)-2-methyl-propyl]amino]methyl]benzoic acid The compound was synthesized using methods A & D as described above followed by deprotection with TFA/DCM (1:1 v/v). Yield: 25 mg (7.9%,); ESI-MS: m/z 267.1 [M+H]$^+$; HPLC (gradient 1): rt 4.19 min (100%); $^1$H-NMR, 400 MHZ, DMSO d6: δ 0.91-1.01 (m, 6H), 2.09-2.2 (m, 1H), 4.03-4.20 (m, 2H), 7.53-7.60 (m, 1H), 7.2 (d, 1H, 3J=7.69 Hz), 7.99 (d, 1H, 3J=7.77 Hz), 8.09-8.16 (m, 1H), 8.83-9.57 (br s, 3H), 11.11 (s, 1H), 13.08 (br s, 1H).

Example 30:3-[[[(1S)-1-Benzyl-2-(hydroxyamino)-2-oxo-ethyl]amino]methyl]benzoic acid The compound was synthesized using methods A & D as described above followed by deprotection with TFA/DCM (1:1 v/v). Yield: 75 mg (27.4%,); ESI-MS: m/z 315.2 [M+H]$^+$; HPLC (gradient 1): rt 6.77 min (100%); $^1$H-NMR, 400 MHZ, DMSO d6: δ 3.00-3.09 (m, 1H), 3.15-3.23 (m, 1H), 3.72-3.82 (m, 1H), 4.10-4.23 (m, 2H), 7.16-7.22 (m, 2H), 7.24-7.34 (m, 3H), 7.53-7.64 (m, 1H), 7.66-7.73 (m, 1H), 7.95-8.03 (m, 1H) 8.1-8.16 (m, 1H), 9.26-9.78 (m, 3H), 10,99 (s, 1H), 13.11 (br s, 1H).

Example 31:3-[[[3-(Hydroxyamino)-3-oxo-propyl]-[(4-methoxyphenyl)methyl]amino]-methyl]benzoic acid The compound was synthesized using methods A, & D as described above followed by deprotection with TFA/DCM (1:1 v/v). Yield: 28 mg (19.5%,); ESI-MS: m/z 359.4 [M+H]$^+$; HPLC (gradient 1): rt 8.21 min (95.4%); $^1$H-NMR, 400 MHZ, DMSO d6: δ 3.00-3.31 (m, 3H), 3.74-3.87 (m, 4H), 4.08-4.57 (m, 4H), 6.93-7.09 (m, 2H), 7.3-7.5 (m, 2H), 7.5-7.67 (m, 1H), 7.67-7.84 (m, 1H), 7.87-8.22 (m, 1H), 8,56-9.4 (m, 1H), 9.67-10.02 (m, 1H), 10.58-10.81 (m, 1H), 13.18 (br s, 1H).

Example 32:3-[[[2-(Hydroxyamino)-1,1-dimethyl-2-oxo-ethyl]amino]methyl]benzoic acid The compound was synthesized using methods A & D as described above followed by deprotection with TFA/DCM (1:1 v/v). Yield: 21 mg (5.5%,); ESI-MS: m/z 253.2 [M+H]$^+$; HPLC (gradient 1): rt 4.19 min (100%); $^1$H-NMR, 400 MHZ, DMSO d6: δ 1.57 (s, 6H), 4.12 (s, 2H), 7.56-7.64 (m, 1H), 7.73 (d, 1H, "J=7.7 Hz), 8.00 (d, 1H, 3J=7.8 Hz), 8.12-8.21 (m, 1H), 9.11-9.14 (m, 2H), 11.17 (s, 1H), 13.21 (br s, 1H).

Example 33:3-{[[(1R)-2-(Hydroxyamino)-1-methyl-2-oxo-ethyl]amino]methyl]benzoic acid The compound was synthesized using methods A & D as described above followed by deprotection with TFA/DCM (1:1 v/v). Yield: 53 mg (24.0%,); ESI-MS: m/z 239.2 [M+H]$^+$; HPLC (gradient 1): rt 3.47 min (100%); $^1$H-NMR, 400 MHZ, DMSO d6: δ 1.38-1.52 (m, 3H), 3.65-3.74 (m, 1H), 4.05-4.31 (m, 2H), 7.55-7.62 (m, 1H), 7.67-7.75 (m, 1H), 7,99 (d, 1H, 3J=7.77 Hz), 8.1-8.17 (m, 1H), 9.05-9.57 (m, 2H), 11.10 (s, 1H), 13.13 (br s, 1H).

Example 34:3-[[[(1R)-1-(Hydroxycarbamoyl)-2-methyl-propyl]amino]methyl]benzoic acid The compound was synthesized using methods A & D as described above followed by deprotection with TFA/DCM (1:1 v/v). Yield: 10 mg (2.6%,); ESI-MS: m/z 267.2 [M+H]$^+$; HPLC (gradient 1): rt 4.29 min (100%); $^1$H-NMR, 400 MHZ, DMSO d6: δ 0.83-1.05 (m, 6H), 2.09-2.22 (m, 1H), 4.00-4.21 (m, 2H), 7.53-7.61 (m, 1H), 7.7 (d1H, 3J=7.57), 7.99 (d, 1H, 3J=7.69), 8.09-8.17 (m, 1H), 8.96-9.55 (m, 2H), 11.11 (s, 1H), 13.09 (br s, 1H).

Example 35:3-[[[(1R)-1-Benzyl-2-(hydroxyamino)-2-oxo-ethyl]amino]methyl]benzoic acid The compound was synthesized using methods A & D as described above followed by deprotection with TFA/DCM (1:1 v/v). Yield: 70 mg (21.3%,); ESI-MS: m/z 315.2 [M+H]$^+$; HPLC (gradient 1): rt 6.75 min (100%); $^1$H-NMR, 400 MHZ, DMSO d6: δ 2.97-3.27 (m, 2H), 3.71-3.81 (m, 1H), 4.04-4.24 (m, 2H), 7.15-7.22 (m, 2H), 7.24-7.38 (m, 3H), 7.53-7.62 (m, 1H), 7.65-7.74 (m, 1H), 7.96-8.02 (m, 1H), 8.11-8.16 (m, 1H), 9.16-9.98 (m, 3H), 10.99 (s, 1H), 13.11 (br s, 1H).

Example 36:3-[[[(1R)-2-(Hydroxyamino)-2-oxo-1-phenyl-ethyl]amino]methyl]benzoic acid The compound was synthesized using methods A & D as described above followed by deprotection with TFA/DCM (1:1 v/v). Yield: 4 mg (1.3%,); ESI-MS: m/z 301.1 [M+H]$^+$; HPLC (gradient 1): rt 6.88 min (100%); $^1$H-NMR, 400 MHZ, DMSO d6: δ 4.00-4-20 (m, 2H), 4.73 (s, 1H), 7.44-7.59 (m, 6H), 7.61-7.68 (m, 1H), 7.96-8.01 (m, 1H), 8.08-8.13 (m, 1H), 9.28-9.41 (m, 1H), 9.81-10.12 (m, 2H), 11.26 (s, 1H), 13.16 (br s, 1H).

Example 37:3-[[[(1S)-2-(Hydroxyamino)-2-oxo-1-phenyl-ethyl]amino]methyl]benzoic acid The compound was synthesized using methods G & D as described above followed by deprotection with TFA/DCM (1:1 v/v). Yield: 26 mg (6.5%,); ESI-MS: m/z 301.2 [M+H]$^+$; HPLC (gradient 1): rt 6.80 min (100%); $^1$H-NMR, 400 MHZ, DMSO d6: δ 4.00-4-20 (m, 2H), 4.74 (s, 1H), 7.45-7.59 (m, 6H), 7.62-7.68 (m, 1H), 7.96-8.01 (m, 1H), 8.08-8.15 (m, 1H), 9.20-9.50 (m, 1H), 9.70-10.20 (m, 2H), 11.28 (s, 1H), 13.16 (br s, 1H).

Example 38:3-[[[4-(hydroxyamino)-4-oxo-butyl]-[(4-methoxyphenyl)methyl]amino]-methyl]benzoic acid The compound was synthesized using methods A & D as described above followed by deprotection with TFA/DCM (1:1 v/v). Yield: 37.4 mg (6.8%,); ESI-MS: m/z 373.4 [M+H]$^+$; HPLC (gradient 1): rt 8.40 min (97.85%); $^1$H-NMR, 400 MHZ, DMSO d6: δ 1.80-2.05 (m, 4H), 2.90-3.05 (m, 2H), 3.75-3.85 (m, 3H), 4.20-4.6 (m, 4H), 6.90-7.10 (m, 2H), 7.35-7.50 (m, 2H), 7.55-7.65 (m, 1H), 7.70-7.80 (m, 1H), 9.95-8.20 (m, 2H), 8,70-9.00 (m, 1H), 9.95-10.10 (m, 1H), 10,52 (s, 1H), 13.20 (br s, 1H).

Example 39:3-[[[(1S)-3-carboxy-1-(hydroxylcarbamoyl)-propyl]amino]methyl]benzoic acid The compound was synthesized using methods A & D as described above followed by deprotection with TFA/DCM (1:1 v/v). Yield: 11 mg (3.1%,); ESI-MS: m/z 297.2 [M+H]$^+$; HPLC (gradient 1): rt 3.63 min (96.5%); $^1$H-NMR, 400 MHZ, DMSO d6: δ 1.88-2.16 (m, 2H), 2.17-2.4 (m, 2H), 3.54-3.68 (m, 1H), 4.01-4.26 (m, 2H), 7.54-7.62 (m, 1H), 7.66-7.75 (m, 1H), 7.94-8.04 (m, 1H), 8.09-8.18 (m, 1H), 9.14-9.67 (m, 2H), 11.09-11.36 (m, 1H), 12.05-12.74 (br s, 1H), 12.76-13.53 (br s, 1H)

Example 40:2-[bis[(3-cyanophenyl)methyl]amino]-ethanehydroxamic acid

The compound was synthesized using methods A & C as described above. Yield: 52 mg (56.5%); ESI-MS: m/z 321.2 [M+H]$^+$; HPLC (gradient 1): rt 11.63 min (98.2%); $^1$H-NMR, 400 MHZ, DMSO d6: δ 3.09 (s, 3H), 3.72-3.89 (m, 4H), 7.53-7.62 (m, 2H), 7.68-7.83 (m, 4H), 7.90-7.98 (m, 2H), 10.62 (br s, 1H)

Example 41:3-[[(3-carbamoylphenyl)methyl-[2-(hydroxyamino)-2-oxo-ethyl]amino]methyl]benzamide The compound was synthesized using methods A & C as described above, starting from 3-(Bromomethyl)benzoic acid methyl ester. Aminolysis of the methyl ester by means of NH$_3$/MeOH was performed prior to final deprotection. Yield: 44 mg (8.2%); ESI-MS: m/z 357.2 [M+H]$^+$; HPLC (gradient 1): rt 4.93 min (98.7%); $^1$H-NMR, 400 MHz, DMSO d6: δ 3.95-4.12 (m, 4H), 4.24-4.47 (m, 2H), 7.42-7.68 (m, 6H), 7.78-8.18 (m, 6H), 9.24-9.42 (m, 1H), 10.56-10.71 (m, 1H)

Example 42: methyl 3-[[(3-carbamoylphenyl)methyl-[2-(hydroxylamino-2-oxo-ethyl]amino]methyl]benzoate Side product of example 41. Yield: 16 mg (2.9%); ESI-MS: m/z 372.3 [M+H]$^+$; HPLC (gradient 1): rt 7.52 min (96.8%); $^1$H-NMR, 400 MHZ, DMSO d6: δ 3.88-3.89 (m, 3H), 3.98-4.15 (m, 4H), 4.26-4.36 (m, 2H), 7.42-7.70 (m, 4H), 7.72-8.17 (m, 6H), 9.32 (br s, 1H), 10.66 (br s, 1H)

Example 43: 3-[[[2-(hydroxyamino)-2-oxo-ethyl]-[(3-methoxycarbonylphenyl)methyl]amino methyl] benzoic acid Side product of example 41. Yield: 10 mg (1.8%); ESI-MS: m/z 373.3 [M+H]$^+$; HPLC (gradient 1): rt 8.69 min (100%); $^1$H-NMR, 400 MHZ DMSO d6: δ 3.87 (s, 3H), 4.06-4.19 (m, 4H), 4.39-4.53 (m, 2H), 7.49-7.59 (m, 2H), 7.67-7.78 (m, 2H), 7.90-8.16 (m, 4H), 10.68 (s, 1H), 13.05 (br s, 1H)

Example 44: 3-[[[(1R)-3-carboxy-1-(hydroxycarbamoyl)-propyl]amino]methyl]benzoic acid The compound was synthesized using methods A & C as described above followed by deprotection with TFA/DCM (1:1 v/v). Yield: 22 mg (8.7%,); ESI-MS: m/z 297.2 [M+H]$^+$; HPLC (gradient 1): rt 3.63 min (95.4%); $^1$H-NMR, 400 MHZ, DMSO d6: δ 1.89-2.17 (m, 2H), 2.19-2.41 (m, 2H), 3.59-3.68 (m, 1H), 3.98-4.29 (m, 2H), 7.54-7.62 (m, 1H), 7.67-7.74 (m, 1H), 7.97-8.02 1H), (m, 8.10-8.16 (m, 1H), 9.03-9.86 (m, 3H), 11.25 (s, 1H), 11.89-13-56 (m, 2H)

Example 45: 3-[[[(1S)-1-(carboxymethyl)-2-(hydroxyamino)-2-oxo-ethyl]amino]methyl]benzoic acid The compound was synthesized using methods A & C as described above followed by deprotection with TFA/DCM (1:1 v/v). Yield: 15 mg (3.1%,); ESI-MS: m/z 283.1 [M+H]$^+$; HPLC (gradient 1): rt 3.36 min (95.1%); $^1$H-NMR, 400 MHZ, DMSO d6: δ 2.69-2.92 (m, 2H), 3.72-3.91 (m, 1H), 3.97-4.31 (m, 2H), 7.52-7.61 (m, 1H), 7.63-7.75 (m, 1H), 7.91-8.02 (m, 1H), 8.03-8.15 (m, 1H), 8.58-9.90 (m, 2H), 11.01-11.29 (m, 1H), 11.34-14.42 (m, 2H)

Example 46: 3-[[[(1R)-1-(carboxymethyl)-2-(hydroxyamino)-2-oxo-ethyl]amino]methyl]benzoic acid The compound was synthesized using methods A & C as described above followed by deprotection with TFA/DCM (1:1 v/v). Yield: 3 mg (0.7%,); ESI-MS: m/z 283.1 [M+H]$^+$; HPLC (gradient 1): rt 3.44 min (93.8%); $^1$H-NMR, 400 MHZ, DMSO d6: δ 2.73-2.90 (m, 2H), 3.78-3.88 (m, 1H), 4.01-4.20 (m, 2H), 7.53-7.61 (m, 1H), 7.64-7.73 (m, 1H), 7.93-8.01 (m, 1H), 8.06-8.14 (m, 1H), 9.05-9.88 (m, 2H), 11.15 (s, 1H), 11.61-14.38 (m, 2H)

Example 47: 2-[bis[(2, 4-difluoro-3-hydroxy-phenyl)-methyl]amino]ethanehydroxamic acid The compound was synthesized using methods A & C as described above. Final deprotection was accomplished using boron tribromide (6 eq) in dichloromethane (10 ml). Yield: 102 mg (58.6%); ESI-MS: m/z 375.5 [M+H]$^+$; HPLC (gradient 1): rt 7.89 min (100%); $^1$H-NMR, 400 MHZ, DMSO d6: δ 3.13 (s, 2H), 4.12-4.28 (m, 4H), 6.87-7.12 (m, 4H), 9.25 (br s, 1H), 10.14 (br s, 2H), 10.45 (br s, 1H)

Example 48: 2-[bis[(3, 5-difluoro-4-hydroxy-phenyl)methyl]-amino]ethanehydroxamic acid The compound was synthesized using methods A & C as described above. Final deprotection was accomplished using boron tribromide (6 eq) in dichloromethane (10 ml). Yield: 105 mg (54%); ESI-MS: m/z 374.9 [M+H]$^+$; HPLC (gradient 1): rt 7.47 min (98.6%); $^1$H-NMR, 400 MHZ, DMSO d6: δ 3.15-3.23 (m, 2H), 3.78-3.99 (m, 4H), 7.12-7.23 (m, 4H), 10.30 (br s, 2H), 10.68 (br s, 1H)

Example 49: 2-[bis[(2, 6-difluoro-3-hydroxy-phenyl) methyl]-amino]ethanehydroxamic acid The compound was synthesized using methods A & C as described above. Final deprotection was accomplished using boron tribromide (6 eq) in dichloromethane (10 ml). Yield: 73 mg (40.8%); ESI-MS: m/z 375.4 [M+H]$^+$; HPLC (gradient 1): rt 9.52 min (100%); $^1$H-NMR, 400 MHZ, DMSO d6: δ 3.08 (s, 2H), 3.85-3.92 (m, 4H), 6.83-6.93 (m, 4H), 9.88 (br s, 2H), 10.05 (br s, 1H)

Example 50: 2-[bis[(4-fluoro-3-hydroxy-phenyl) methyl]-amino]ethanehydroxamic acid The compound was synthesized using methods A & C as described above. Final deprotection was accomplished using boron tribromide (6 eq) in dichloromethane (10 ml). Yield: 59 mg (39.6%); ESI-MS: m/z 339.1 [M+H]$^+$; HPLC (gradient 1): rt 7.36 min (100%); $^1$H-NMR, 400 MHZ, DMSO d6: δ 3.28 (s, 2H), 3.72-4.11 (m, 4H), 6.87-6.98 (m, 2H), 7.04-7.24 (m, 4H), 8.70-9.58 (m, 1H), 9.80-10.27 (m, 2H), 10.53-10.84 (m, 1H)

Example 51: 2-[bis[(2-fluoro-3-hydroxy-phenyl) methyl]-amino]ethanehydroxamic acid The compound was synthesized using methods A & C as described above. Final deprotection was accomplished using boron tribromide (6 eq) in dichloromethane (10 ml). Yield: 63 mg (75.7%); ESI-MS: m/z 339.1 [M+H]$^+$; HPLC (gradient 1): rt 6.83 min (100%); $^1$H-NMR, 400 MHZ, DMSO d6: δ 3.20 (s, 2H), 3.97 (s, 4H), 6.86-7.08 (m, 6H), 9.20-9.42 (m, 1H), 9.71-10.14 (m, 2H), 10.51 (br s, 1H)

Example 52: 2-[bis[(4-chloro-2-fluoro-3-hydroxyphenyl)-methyl]amino]ethanehydroxamic acid The compound was synthesized using methods A & C as described above. Final deprotection was accomplished using boron tribromide (6 eq) in dichloromethane (10 ml). Yield: 62 mg (56.4%); ESI-MS: m/z 406.9 [M+H]$^+$; HPLC (gradient 1): rt 10.48 min (100%); $^1$H-NMR, 400 MHZ, DMSO d6: δ 3.10 (s, 2H), 3.85 (s, 4H), 6.95-6.98 (m, 2H), 7.16-7.24 (m, 2H), 10.10-10.60 (m, 3H)

Example 53: 2-[(2, 4-difluoro-3-hydroxy-phenyl) methyl-[(4-methoxyphenyl)methyl]amino]ethanehydroxamic acid The compound was synthesized using methods A, D & F as described above. Final deprotection was accomplished using boron tribromide (6 eq) in dichloromethane (10 ml). Yield: 66 mg (35.7%); ESI-MS: m/z 353.1 [M+H]$^+$; HPLC (gradient 1): rt 8.37 min (100%); $^1$H-NMR, 400 MHZ, DMSO d6: δ 3.32 (s, 2H), 3.77 (s, 3H), 4.07-4.10 (m, 3H), 4.35-4.41 (m, 1H), 6.96-7.14 (m, 4H), 7.39-7.49 (m, 2H), 9.05-9.60 (m, 1H), 10.26-10.41 (m, 1H), 10.62-10.76 (m, 1H)

Example 54: ethyl 3-[[(3-ethoxycarbonylphenyl)methyl-[2-(hydroxyamino)-2-oxo-ethyl]amino]methyl]benzoate The compound was synthesized using methods A & C as described above. Yield: 50 mg (8%); ESI-MS: m/z 415.0 [M+H]$^+$; HPLC (gradient 1): rt 12.93 min (100%); $^1$H-NMR, 400 MHz, DMSO d6: δ 1.32-1.35 (m, 6H), 3.18-3.40 (m, 2H), 3.90-4.08 (m, 4H), 4.30-4.36 (m, 4H), 7.48-7.56 (m, 2H), 7.64-7.75 (m, 2H), 7.86-8.10 (m, 4H), 10.59 (br S, 1H)

Example 55: 2-[bis[(4-cyanophenyl)methyl]amino]-ethanehydroxamic acid

The compound was synthesized using methods A & C as described above. Yield: 30 mg (9.3%); ESI-MS: m/z 321.0 [M+H]$^+$; HPLC (gradient 1): rt 12.83 min (100%); $^1$H-NMR, 400 MHZ, DMSO d6: δ 3.05 (s, 2H), 3.84 (s, 4H), 7.61-7.63 (m, 4H), 7.80-7.83 (m, 4H), 10.51 (br s, 1H)

Example 56: 2-[bis[(4-chloro-2-fluoro-3-methoxy-phenyl)-methyl]amino]ethanehydroxamic acid The compound was synthesized using methods A & C as described above. Yield: 33 mg (8.5%); ESI-MS: m/z 435.9 [M+H]$^+$; HPLC (gradient 1): rt 17.12 min (99.3%); $^1$H-NMR, 400 MHZ, DMSO d6: δ 3.11 (s, 2H), 3.83 (s, 4H), 3.85 (s, 6H), 7.24-7.30 (m, 4H), 10.43 (br s, 1H)

Example 57: 3-[bis[(4-cyanophenyl)methyl]amino]-propanehydroxamic acid

The compound was synthesized using methods A & C as described above. Yield: 65 mg (19.6%); ESI-MS: m/z 335.0 [M+H]$^+$; HPLC (gradient 1): rt 9.01 min (100%); TH-NMR, 400 MHZ, DMSO d6: δ 2,30-2,34 (m, 2H), 2.80 (br s, 2H), 3.85 (br s, 4H), 7.59-7.61 (m, 4H), 7.83-7.85 (m, 4H), 10.49 (br s, 1H)

Example 58: 2-[bis[(2, 4-difluoro-3-methoxy-phenyl)methyl]-amino]ethanehydroxamic acid The compound was synthesized using methods A & C as described above. Yield: 26 mg (6.4%); ESI-MS: m/z 403.0 [M+H]$^+$; HPLC (gradient 1): rt 14.45 min (100%); $^1$H-NMR, 400 MHZ, DMSO d6: δ 3.18 (s, 2H), 3.82 (s, 4H), 3.89 (s, 6H), 7.08-7.13 (m, 2H), 7.20-7.25 (m, 2H), 10.43 (br s, 1H)

Example 59: 3-[[(3-ethoxycarbonylphenyl)methyl-[2-(hydroxyamino)-2-oxo-ethyl]amino]methyl]benzoic acid The compound was synthesized using methods A, D & F as described above. Yield: 77 mg ESI-MS: 387.0 HPLC (16.3%); m/z[M+H]$^+$; (gradient 1): rt 9.84 min (98.2%); $^1$H-NMR, 400 MHZ, DMSO d6: δ 1.34 (t, 3H, 3J=7.1 Hz), 3.26 (s, 2H), 3.84-4.24 (m, 4H), 4.33 (q, 2H, 3J=7.1 Hz), 7.49-7.63 (m, 2H), 7.67-7.83 (m, 2H), 7.90-8.15 (m, 4H), 9.28-9.55 (m, 1H), 10.52-10.66 (m, 1H), 13.04 (br s, 1H)

Example 60: 2-[bis[(4-chloro-2-fluoro-phenyl)methyl]-amino]ethanehydroxamic acid The compound was synthesized using methods A & C as described above. Yield: 22 mg (5.8%); ESI-MS: m/z 375.9 [M+H]$^+$; HPLC (gradient 1): rt 17.44 min (100%); $^1$H-NMR, 400 MHZ, DMSO d6: δ 3.08 (s, 2H), 3.82 (s, 4H), 7.28 (dd, 2H, 4J=1.7 Hz, 3J=8.3 Hz), 7.38 (dd, 2H, 4J=1.7 Hz, 3J=10.0 Hz), 7.53-7.57 (m, 2H), 10.44 (br s 1H)

Example 61: 2-[bis[(3, 4, 5-trimethoxyphenyl)methyl]-amino]-ethanehydroxamic acid The compound was synthesized using methods A & C as described above. Yield: 29 mg (6.4%); ESI-MS: m/z 450.9 [M+H]$^+$; HPLC (gradient 1): rt 10.17 min (100%); $^1$H-NMR, 400 MHZ, DMSO d6: δ 3.45 (br s, 2H), 3.67 (s, 6H), 3.79 (s, 12H), 4.13-4.36 (m, 4H), 6.79-6.84 (m, 4H), 10.90 (br s, 1H)

Example 62: 3-[bis[(4-chloro-2-fluoro-phenyl)methyl]-amino]propanehydroxamic acid The compound was synthesized using methods A & C as described above. Yield: 97 mg (24.9%); ESI-MS: m/z 389.0 [M+H]$^+$; HPLC (gradient 1): rt 11.59 min (99.5%); $^1$H-NMR, 400 MHZ, DMSO d6: δ 2.34 (s, 2H), 2.87 (br s, 2H), 3.86-4.41 (m, 4H), 7.31-7.55 (m, 6H), 10.51 (br s, 1H)

Example 63: 2-[bis(2, 3-dihydro-1, 4-benzodioxin-6-yl-methyl)amino]ethanehydroxamic acid The compound was synthesized using methods G & H as described above. Yield: 35 mg (10.9%); ESI-MS: m/z 387.1 [M+H]$^+$; HPLC (gradient 1): rt 9.75 min (97.7%); $^1$H-NMR, 400 MHZ, DMSO d6: δ 3.41 (br s, 2H), 4.12 (br s, 4H), 4.26 (s, 8H), 6.89-6.99 (m, 4H), 7.04-7.09 (m, 2H), 10.88 (br s, 1H)

Example 64: 3-[bis[(2, 4-difluoro-3-methoxy-phenyl)methyl]-amino]propanehydroxamic acid The compound was synthesized using methods A & C as described above. Yield: 43 (10.2%); mg ESI-MS: m/z 416.9 [M+H]$^+$; HPLC (gradient 1): rt 10.85 min (100%); $^1$H-NMR, 400 MHZ, DMSO d6: δ 2.38 (br s, 2H), 2.96 (br s, 2H), 3.91-4.09 (m, 12H), 7.17-7.23 (m, 4H), 10.57 (br s, 1H)

Example 65: 3-[bis[(4-chloro-2-fluoro-3-methoxy-phenyl)-methyl]amino]propanehydroxamic acid The compound was synthesized using methods A & C as described above. Yield: 57 mg (12.8%); ESI-MS: m/z 449.0 [M+H]$^+$; HPLC (gradient 1): rt 12.52 min (100%); $^1$H-NMR, 400 MHZ, DMSO d6: δ 2.35 (br s, 2H), 2.93 (br s, 2H), 3.87-3.92 (m, 10H), 7.23-7.33 (m, 4H), 10.53 (br s, 1H)

Example 66: 3-[bis[(3, 4, 5-trimethoxyphenyl)methyl]amino]-propanehydroxamic acid The compound was synthesized using methods A & C as described above. Yield: 67 mg (14.4%); ESI-MS: m/z 465.2 [M+H]$^+$; HPLC (gradient 1): rt 9.57 min (100%); $^1$H-NMR, 400 MHZ, DMSO d6: δ 2.58 (br s, 2H), 3.28 (br s, 2H), 3.68 (s, 6H), 3.79 (s, 12H), 4.28-4.35 (m, 4H), 6.82 (s, 4H), 10.72 (br s, 1H)

Example 67: 2-(dibenzylamino) ethanehydroxamic acid

The compound was synthesized using methods G & H as described above. Yield: 15 mg (26%); ESI-MS: m/z 271.1

[M+H]⁺; HPLC (gradient 1): rt 8.64 min (100%); $^1$H-NMR, 400 MHZ, DMSO d6: δ 3.32 (br s, 2H), 4.10-4.40 (m, 4H), 7.37-7.56 (m, 10H), 10.74 (br s, 1H)

Example 68:2-[bis[(7-methoxy-1, 3-benzodioxol-5-yl)methyl]amino]ethanehydroxamic acid The compound was synthesized using methods G & H as described above. Yield: 59 (36.5%); ESI-MS: mg m/z 419.1 [M+H]⁺; HPLC (gradient 1): rt 10.29 min (100%); $^1$H-NMR, 400 MHZ, DMSO d6: δ 3.39 (br s, 2H), 3.84 (s, 6H), 4.08 (br s, 4H), 6.03-6.05 (m, 4H), 6.78-6.85 (m, 4H), 10.87 (br s, 1H)

Example 69:3-[bis(2, 3-dihydro-1, 4-benzodioxin-6-ylmethyl)amino]propanehydroxamic acid The compound was synthesized using methods G & H as described above. Yield: 43 mg (43.7%); ESI-MS: m/z 401.2 [M+H]⁺; HPLC (gradient 1): rt 9.92 min (100%); $^1$H-NMR, 400 MHZ, DMSO d6: δ 3.15 (br s, 2H), 3.85 (br s, 4H), 4.19-4.27 (m, 8H), 6.94-7.03 (m, 6H), 9.63 (br s, 1H), 10.71 (br s, 1H)

Example 70:3-[bis[(3-cyanophenyl)methyl]amino]-propanehydroxamic acid

The compound was synthesized using methods A & C as described above. Yield: 44 mg (13.2%); ESI-MS: m/z 335.2 [M+H]⁺; HPLC (gradient 1): rt 9.92 min (100%); $^1$H-NMR, 400 MHZ, DMSO d6: δ 2.37 (br s, 2H), 2.89 (br s, 2H), 3.99-4.53 (m, 8H), 7.58-7.98 (m, 8H), 10.55 (br s, 1H)

Example 71:3-(dibenzylamino) propanehydroxamic acid

The compound was synthesized using methods G & H as described above. Yield: 22
ESI-MS: m/z 285.1 [M+H]⁺; HPLC (31.2%); mg rt 8.77 min (100%); $^1$H-NMR, 400 MHZ, DMSO d6: (gradient 1): 4.21-4.30 2H), 2H, 3J=6.8 Hz), 3.27-3.35 (m, 2.54-2.57 (t, m, 4H), 7.45-7.48 (m, 10H), 9.97 (br s, 1H)

Example 72:2-[bis[[3-(difluoromethoxy)phenyl]methyl]-aminolethanehydroxamic acid The compound was synthesized using methods A & C as described above. Yield: 58 mg (10%); ESI-MS: m/z 403.1 [M+H]⁺; HPLC (gradient 1): rt 13.68 min (100%); $^1$H-NMR, 400 MHZ, DMSO d6: δ 3.16 (s, 2H), 3.78-3.95 (m, 4H), 7.04-7.47 (m, 9H), 10.61 (br s, 1H)

Example 73:2-[bis(3-pyridylmethyl)amino]ethane-hydroxamic acid

The compound was synthesized using methods G & H as described above. Yield: 30 mg (28.8%); ESI-MS: m/z 273.1 [M+H]⁺; HPLC (gradient 3): rt 2.35 min (100%); $^1$H-NMR, 400 MHZ, DMSO d6: δ 3.16 (s, 2H), 3.97 (s, 4H), 7.82-7.85 (dd, 2H, 4J=2.0 Hz, 3J=5.9 Hz), 8.38-8.40 (m, 2H), 8.66-8.67 (m, 2H), 8.87 (s, 2H)

Example 74:3-[bis(1, 3-benzodioxol-5-ylmethyl)amino]-propanehydroxamic acid

The compound was synthesized using methods A & C as described above. Yield: 83 mg (22. 3%); ESI-MS: m/z 373.2 [M+H]⁺; HPLC (gradient 1): rt 9.49 min (100%); $^1$H-NMR, 400 MHZ, DMSO d6: δ 2.51-2.55 (t, 2H, 3J=6.8 Hz), 3.26-3.39 (m, 2H), 4.16-4.19 (m, 4H), 6.01 (s, 4H), 6.88-6.96 (m, 6H), 9.90 (br s, 1H)

Analytical Methods

HPLC: The analytical HPLC-system consisted of a Merck-Hitachi device (model LaChrom) utilizing a LUNA RP 18 (5 µm), analytical column (length: 125 mm, diameter: 4 mm), and a diode array detector (DAD) with A=214 nm as the reporting wavelength. The compounds were analyzed using a gradient at a flow rate of 1 mL/min; whereby eluent (A) was acetonitrile, eluent (B) was water, both containing 0.04% (v/v) trifluoroacetic acid applying one of the following gradients:
Gradient 1:0 min-5 min->5% (A), 5 min-15 min->5-60% (A), 15 min-20 min 60-95% (A) 20 min-30 min 95% (A)
Gradient 2:0 min-15 min 5-50% (A), 15 min-20 min->50-95% (A), 20 min-23 min 95% (A)
Gradient 3:0 min-5 min 1% (A), 5 min-20 min->1-20% (A), 20 min-30 min 20-95% (A), 30 min-34 min 95% (A)
The purities of all reported compounds were determined by the percentage of the peak area at 214 nm.

Mass-spectrometry, NMR-spectroscopy: ESI-Mass spectra were obtained with a SCIEX API 1200 spectrometer (Perkin Elmer) or an expressionCMS (Advion). The 1H NMR-Spectra were recorded at an Agilent DD2 400-MHz spectrometer. Chemical shifts (d) are expressed as parts per million (ppm) downfield from tetramethylsilane. Splitting patterns have been designated as follows: s (singlet), d (doublet), dd (doublet of doublet), t (triplet), m (multiplet) and br (broad signal).

Enzymatic Assays

The determination of enzymatic activity was based on the cleavage of internally quenched peptide substrates. A typical assay of 250 µl total volume measured in black 96 well plates consisted of 100 µl buffer, 50 µl enzyme at a final concentration of 5e-8 M to 5e-9 M, 50 µl substrate (0.15 to 80 µM, in buffer, 0.5% DMSO) and 50 µl inhibitor solution (in buffer, 1% DMSO). In case of 125 µl assay volume (black 96 half area well plates) all volumes were cut in half. Enzymatic activity of ADAMs was measured in 384 well plates with 60 µl total assay volume consisting of 20 µl inhibitor, 20 µl buffer, 10 µl enzyme and 10 µl substrate.

Ki values were assessed combining 4 substrate concentrations (5-40 µM) with at least 5 inhibitor concentrations. For IC50 values the influence of 12 inhibitor concentrations ranging from 0 to 5e-5 M on the enzymatic activity was investigated in the presence of one standard substrate concentration (10 µM). Initial velocities were determined and converted into concentration units applying a standard curve obtained after complete conversion of different substrate concentrations under assay conditions. All measurements were performed using a fluorescence plate reader (FLUOstar OPTIMA, BMG Labtech) at 30° C. The kinetic parameters were determined at least in duplicates on separate days. The excitation/emission wavelength was 340/420 nm. The kinetic data was evaluated using GraFit software (version 7.0.3, Erithacus Software).

MMPs were activated prior to measurement by APMA (p-aminophenylmercuric acetate) treatment according to manufacturer's instructions (R&D systems).

TABLE 1

| Peptide substrates and assay conditions used for determination of enzymatic activity | | | |
|---|---|---|---|
| Enzyme | Substrate | Buffer | Assay volume |
| hMeprin β | Abz-YVAEAPK(Dnp)G-OH | 40 mM Tris pH 8.0 | 250 μl |
| hMeprin α | Abz-YVADAPK(Dnp)G-OH | 40 mM HEPES pH 7.4 | 250 μl |
| hMMPs 2, 9 and 13 (R&D systems) | Mca-PLGL-(DapDnp)-AR-NH$_2$ | 50 mM Tris, 2 μM ZnCl$_2$, 150 mM NaCl, pH 7.5 | 125 μl |
| hADAMs 10 and 17 (R&D systems) | Abz-LANAVRSSSR-(DapDnp)-NH$_2$ | 25 mM Tris, 2 μM ZnCl$_2$, 150 mM NaCl, pH 9.0 | 60 μl |

(Abz = 2-aminobenzoyl; Dnp = 2,4-dinitrophenyl; Mca = 7-methoxy coumarin; Dap = 2,3-diaminopropionic acid; hMeprin = human meprin; hMMPs = human Matrix Metalloproteases, hADAMs = human A Desintegrin and Metalloproteases)

Inhibition of Meprin Beta and Alpha

The following compounds according to the present invention were synthesized using the above general procedures. IC50 and Ki values for the inhibition of Meprin β and α measured using the above enzyme assays are shown in the following Tables. IC50 refers to the average IC50 values measured as described above, SD (IC50) refers to the standard deviation of the average IC50 values, Ki refers to the average K; values measured as described above, and SD (Ki) to the standard deviation of the average Ki values.

TABLE 2

| Compounds of Formula V (Series 4) | | | | | | | | | |
|---|---|---|---|---|---|---|---|---|---|
| | | Meprin Beta | | | | Meprin Alpha | | | |
| Structure | Cpd ID | IC50 [nM] | SD (IC50) [nM] | Ki [nM] | SD (Ki) [nM] | IC50 [nM] | SD (IC50) [nM] | Ki [nM] | SD (Ki) [nM] |
| (structure) | Example 1 | 468 | 49 | 223 | 15 | 85700 | 400 | n.d. | n.d. |
| (structure) | Example 2 | 50 | 17 | 18 | 3 | 30950 | 4313 | 10410 | 999 |

TABLE 2-continued

Compounds of Formula V (Series 4)

| Structure | Cpd ID | Meprin Beta | | | | Meprin Alpha | | | |
| --- | --- | --- | --- | --- | --- | --- | --- | --- | --- |
| | | IC50 [nM] | SD (IC50) [nM] | Ki [nM] | SD (Ki) [nM] | IC50 [nM] | SD (IC50) [nM] | Ki [nM] | SD (Ki) [nM] |
| 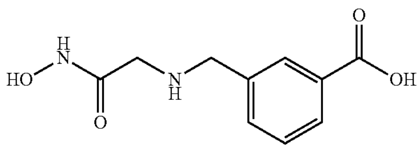 [SMILES: O=C(CNCc1cccc(C(=O)O)c1)NO] | Example 3 | 377 | 14 | 183 | 18 | n.d. | n.d. | n.d. | n.d. |
| 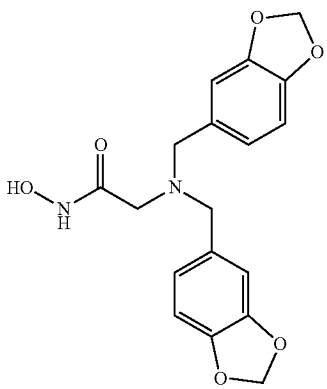 [SMILES: O=C(CN(Cc1ccc2c(c1)OCO2)Cc1ccc2c(c1)OCO2)NO] | Example 4 | 5363 | 2312 | 6555 | 509 | 830 | 47 | 274 | 63 |
| 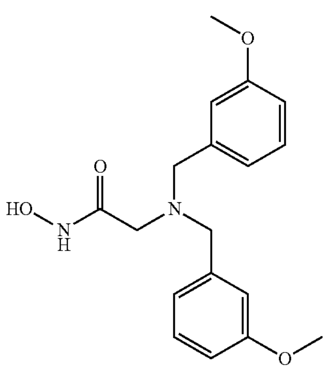 [SMILES: COc1cccc(CN(CC(=O)NO)Cc2cccc(OC)c2)c1] | Example 5 | 25600 | 6023 | 15664 | 1119 | n.d. | n.d. | n.d. | n.d. |
| 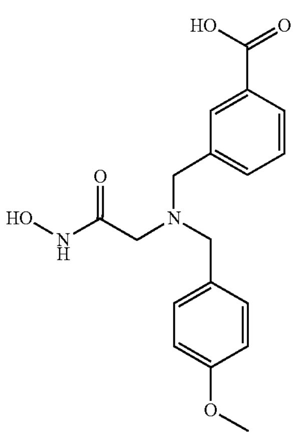 [SMILES: COc1ccc(CN(CC(=O)NO)Cc2cccc(C(=O)O)c2)cc1] | Example 6 | 76 | 17 | 39 | 0.2 | 3435 | 134 | 1210 | 14 |

TABLE 2-continued

Compounds of Formula V (Series 4)

| Structure | Cpd ID | Meprin Beta | | | | Meprin Alpha | | | |
| --- | --- | --- | --- | --- | --- | --- | --- | --- | --- |
| | | IC50 [nM] | SD (IC50) [nM] | Ki [nM] | SD (Ki) [nM] | IC50 [nM] | SD (IC50) [nM] | Ki [nM] | SD (Ki) [nM] |
| *(structure)* | Example 7 | 206 | 32 | 101 | 7 | 44400 | 4526 | n.d. | n.d. |
| *(structure)* | Example 8 | 1445 | 630 | 1034 | 292 | n.d. | n.d. | n.d. | n.d. |
| *(structure)* | Example 9 | 2250 | 982 | 874 | 156 | n.d. | n.d. | n.d. | n.d. |
| *(structure)* | Example 10 | 352 | 40 | 157 | 15 | 3735 | 714 | 1091 | 227 |

TABLE 2-continued

Compounds of Formula V (Series 4)

| Structure | Cpd ID | Meprin Beta | | | | Meprin Alpha | | | |
| --- | --- | --- | --- | --- | --- | --- | --- | --- | --- |
| | | IC50 [nM] | SD (IC50) [nM] | Ki [nM] | SD (Ki) [nM] | IC50 [nM] | SD (IC50) [nM] | Ki [nM] | SD (Ki) [nM] |
| | Example 11 | 355 | 46 | 154 | 2 | 2120 | 283 | 1255 | 346 |
| | Example 12 | 31350 | 636 | n.d. | n.d. | n.d. | n.d. | n.d. | n.d. |
| | Example 13 | 41100 | 4000 | n.d. | n.d. | n.d. | n.d. | n.d. | n.d. |
| | Example 14 | 559 | 32 | 288 | 27 | n.d. | n.d. | n.d. | n.d. |

TABLE 2-continued

Compounds of Formula V (Series 4)

| Structure | Cpd ID | Meprin Beta | | | | Meprin Alpha | | | |
| --- | --- | --- | --- | --- | --- | --- | --- | --- | --- |
| | | IC50 [nM] | SD (IC50) [nM] | Ki [nM] | SD (Ki) [nM] | IC50 [nM] | SD (IC50) [nM] | Ki [nM] | SD (Ki) [nM] |
| (structure) | Example 15 | 31800 | 1600 | n.d. | n.d. | n.d. | n.d. | n.d. | n.d. |
| (structure) | Example 16 | 22800 | 4384 | n.d. | n.d. | n.d. | n.d. | n.d. | n.d. |
| (structure) | Example 17 | 1285 | 15 | 797 | 185 | n.d. | n.d. | n.d. | n.d. |

TABLE 2-continued

Compounds of Formula V (Series 4)

| Structure | Cpd ID | Meprin Beta | | | | Meprin Alpha | | | |
| --- | --- | --- | --- | --- | --- | --- | --- | --- | --- |
| | | IC50 [nM] | SD (IC50) [nM] | Ki [nM] | SD (Ki) [nM] | IC50 [nM] | SD (IC50) [nM] | Ki [nM] | SD (Ki) [nM] |
| (structure) | Example 18 | 361 | 35 | 170 | 11 | 4670 | 1 | 1990 | 481 |
| (structure) | Example 19 | 320 | 7 | 125 | 16 | 4875 | 615 | 1950 | 28 |
| (structure) | Example 20 | 76 | 4 | 33 | 5 | 1795 | 205 | 796 | 55 |

TABLE 2-continued

Compounds of Formula V (Series 4)

| Structure | Cpd ID | Meprin Beta | | | | Meprin Alpha | | | |
| --- | --- | --- | --- | --- | --- | --- | --- | --- | --- |
| | | IC50 [nM] | SD (IC50) [nM] | Ki [nM] | SD (Ki) [nM] | IC50 [nM] | SD (IC50) [nM] | Ki [nM] | SD (Ki) [nM] |
| (3-carboxybenzyl)(4-fluorobenzyl)-N-hydroxyacetamide structure | Example 21 | 177 | 8 | 1680 | 99 | 4215 | 460 | 1680 | 99 |
| (3-carboxybenzyl)(benzo[d][1,3]dioxol-5-ylmethyl)-N-hydroxyacetamide structure | Example 22 | 285 | 94 | 105 | 4 | 1430 | 255 | 606 | 45 |
| (benzo[d][1,3]dioxol-5-ylmethyl)(4-methoxybenzyl)-N-hydroxyacetamide structure | Example 23 | 20000 | 0 | n.d. | n.d. | 1685 | 36 | n.d. | n.d. |

TABLE 2-continued

Compounds of Formula V (Series 4)

| Structure | Cpd ID | Meprin Beta | | | | Meprin Alpha | | | |
| --- | --- | --- | --- | --- | --- | --- | --- | --- | --- |
| | | IC50 [nM] | SD (IC50) [nM] | Ki [nM] | SD (Ki) [nM] | IC50 [nM] | SD (IC50) [nM] | Ki [nM] | SD (Ki) [nM] |
| 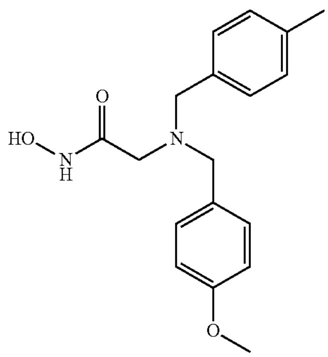 [SMILES: COc1ccc(CN(CC(=O)NO)Cc2ccc(C)cc2)cc1] | Example 24 | 60933 | 2065 | n.d. | n.d. | 2330 | 283 | n.d. | n.d. |
| 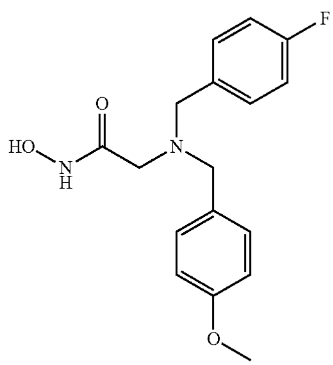 [SMILES: COc1ccc(CN(CC(=O)NO)Cc2ccc(F)cc2)cc1] | Example 25 | 80400 | 707 | n.d. | n.d. | 4135 | 347 | n.d. | n.d. |
| 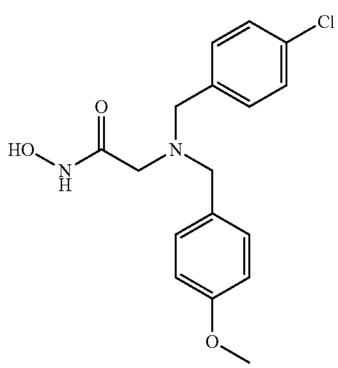 [SMILES: COc1ccc(CN(CC(=O)NO)Cc2ccc(Cl)cc2)cc1] | Example 26 | 53400 | 3536 | n.d. | n.d. | 1985 | 148 | n.d. | n.d. |
| 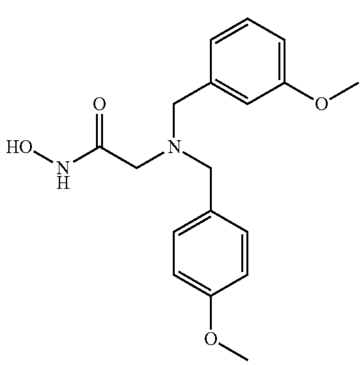 [SMILES: COc1ccc(CN(CC(=O)NO)Cc2cccc(OC)c2)cc1] | Example 27 | 34450 | 2899 | n.d. | n.d. | 3195 | 2474 | n.d. | n.d. |

TABLE 2-continued
| | | Meprin Beta | | | | Meprin Alpha | | | |
|---|---|---|---|---|---|---|---|---|---|
| Structure | Cpd ID | IC50 [nM] | SD (IC50) [nM] | Ki [nM] | SD (Ki) [nM] | IC50 [nM] | SD (IC50) [nM] | Ki [nM] | SD (Ki) [nM] |
| 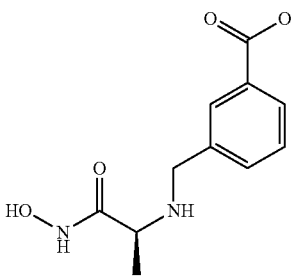 | Example 28 | 4200 | 495 | 3103 | 422 | 16700 | 265 | n.d. | n.d. |
| 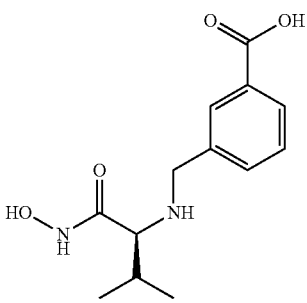 [SMILES: CC(C)[C@H](NCc1cccc(C(=O)O)c1)C(=O)NO] | Example 29 | 15800 | 2687 | n.d. | n.d. | 44367 | 5424 | n.d. | n.d. |
| 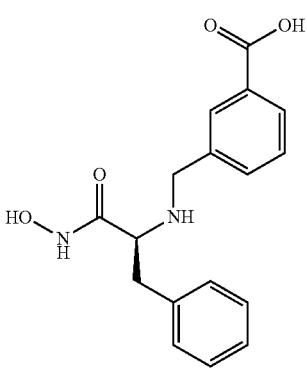 [SMILES: O=C(O)c1cccc(CN[C@@H](Cc2ccccc2)C(=O)NO)c1] | Example 30 | 15500 | 990 | n.d. | n.d. | 10245 | 361 | n.d. | n.d. |
| 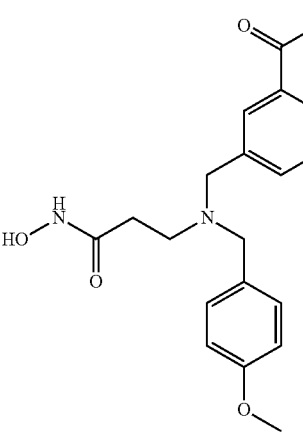 | Example 31 | 643 | 30 | 165 | 11 | 233 | 36 | 87 | 2 |

TABLE 2-continued

Compounds of Formula V (Series 4)

| Structure | Cpd ID | Meprin Beta | | | | Meprin Alpha | | | |
| --- | --- | --- | --- | --- | --- | --- | --- | --- | --- |
| | | IC50 [nM] | SD (IC50) [nM] | Ki [nM] | SD (Ki) [nM] | IC50 [nM] | SD (IC50) [nM] | Ki [nM] | SD (Ki) [nM] |
| (structure) | Example 32 | 39300 | 1556 | n.d. | n.d. | 265500 | 4950 | n.d. | n.d. |
| (structure) | Example 33 | 4255 | 163 | 2575 | 21 | 45150 | 1344 | n.d. | n.d. |
| (structure) | Example 34 | 11850 | 212 | n.d. | n.d. | 29950 | 778 | n.d. | n.d. |
| (structure) | Example 35 | 2910 | 141 | 1355 | 64 | 2655 | 247 | n.d. | n.d. |

TABLE 2-continued

Compounds of Formula V (Series 4)

| Structure | Cpd ID | Meprin Beta | | | | Meprin Alpha | | | |
| --- | --- | --- | --- | --- | --- | --- | --- | --- | --- |
| | | IC50 [nM] | SD (IC50) [nM] | Ki [nM] | SD (Ki) [nM] | IC50 [nM] | SD (IC50) [nM] | Ki [nM] | SD (Ki) [nM] |
| 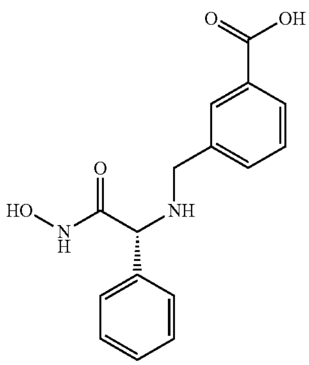 [SMILES: O=C(O)c1cccc(CN[C@@H](C(=O)NO)c2ccccc2)c1] | Example 36 | 11650 | 354 | n.d. | n.d. | 21700 | 1414 | n.d. | n.d. |
| 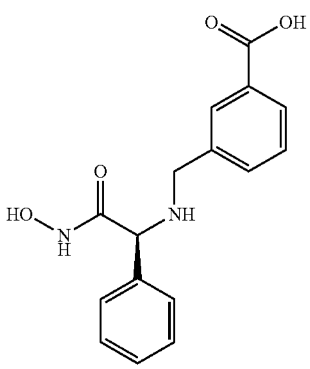 [SMILES: O=C(O)c1cccc(CN[C@H](C(=O)NO)c2ccccc2)c1] | Example 37 | 12150 | 71 | n.d. | n.d. | 26250 | 354 | n.d. | n.d. |
| 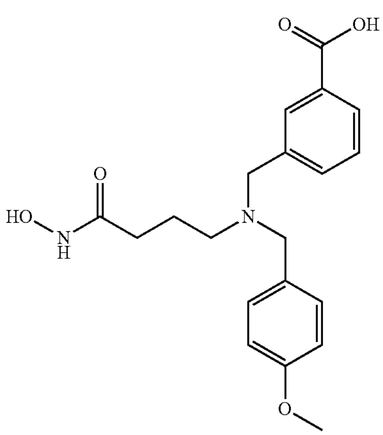 [SMILES: COc1ccc(CN(CCCC(=O)NO)Cc2cccc(C(=O)O)c2)cc1] | Example 38 | 742 | 42 | 225 | 27 | 2610 | 283 | 948 | 22 |

TABLE 2-continued

| | | Meprin Beta | | | | Meprin Alpha | | | |
|---|---|---|---|---|---|---|---|---|---|
| Structure | Cpd ID | IC50 [nM] | SD (IC50) [nM] | Ki [nM] | SD (Ki) [nM] | IC50 [nM] | SD (IC50) [nM] | Ki [nM] | SD (Ki) [nM] |
| (structure) | Example 39 | 654 | 11 | 325 | 10 | 8660 | 552 | 2530 | 311 |
| (structure) | Example 40 | 12000 | 566 | n.d. | n.d. | 1465 | 120 | 521 | 8 |
| (structure) | Example 41 | 13100 | 849 | n.d. | n.d. | 2900 | 156 | 852 | 66 |
| (structure) | Example 42 | 25000 | 1100 | n.d. | n.d. | 3545 | 177 | 1190 | 28 |

Compounds of Formula V (Series 4)

TABLE 2-continued

Compounds of Formula V (Series 4)

| | | Meprin Beta | | | | Meprin Alpha | | | |
|---|---|---|---|---|---|---|---|---|---|
| Structure | Cpd ID | IC50 [nM] | SD (IC50) [nM] | Ki [nM] | SD (Ki) [nM] | IC50 [nM] | SD (IC50) [nM] | Ki [nM] | SD (Ki) [nM] |
| | Example 43 | 516 | 8 | 152 | 1 | 6275 | 148 | 1735 | 78 |
| | Example 44 | 768 | 40 | 277 | 23 | 32100 | 1697 | n.d. | n.d. |
| | Example 45 | 1325 | 92 | 644 | 12 | 60400 | 2546 | n.d. | n.d. |
| | Example 46 | 548 | 25 | 254 | 18 | 15100 | 1838 | n.d. | n.d. |

TABLE 2-continued

Compounds of Formula V (Series 4)

| Structure | Cpd ID | Meprin Beta | | | | Meprin Alpha | | | |
|---|---|---|---|---|---|---|---|---|---|
| | | IC50 [nM] | SD (IC50) [nM] | Ki [nM] | SD (Ki) [nM] | IC50 [nM] | SD (IC50) [nM] | Ki [nM] | SD (Ki) [nM] |
| 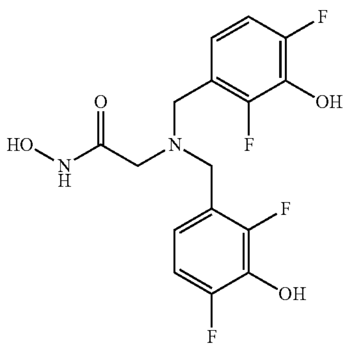 [SMILES: O=C(CN(Cc1ccc(F)c(O)c1F)Cc1ccc(F)c(O)c1F)NO] | Example 47 | 23 | 1 | 12 | 2 | 626 | 1 | 189 | 15 |
| 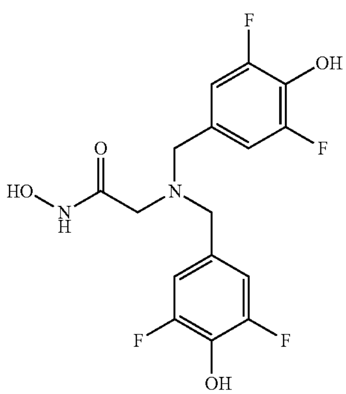 [SMILES: O=C(CN(Cc1cc(F)c(O)c(F)c1)Cc1cc(F)c(O)c(F)c1)NO] | Example 48 | 272 | 20 | 118 | 7 | 1305 | 120 | 263 | 6 |
| 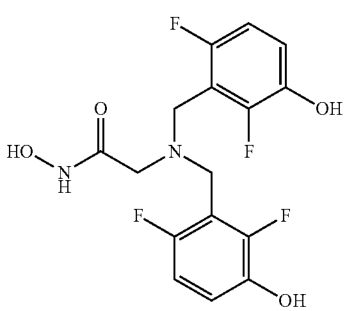 [SMILES: O=C(CN(Cc1c(F)ccc(O)c1F)Cc1c(F)ccc(O)c1F)NO] | Example 49 | 5515 | 78 | 1965 | 64 | 5600 | 156 | 998 | 1 |
| 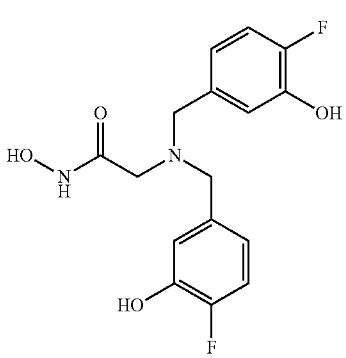 [SMILES: O=C(CN(Cc1ccc(F)c(O)c1)Cc1ccc(F)c(O)c1)NO] | Example 50 | 1060 | 57 | 352 | 8 | 986 | 21 | 306 | 14 |

TABLE 2-continued

Compounds of Formula V (Series 4)

| Structure | Cpd ID | Meprin Beta | | | | Meprin Alpha | | | |
| --- | --- | --- | --- | --- | --- | --- | --- | --- | --- |
| | | IC50 [nM] | SD (IC50) [nM] | Ki [nM] | SD (Ki) [nM] | IC50 [nM] | SD (IC50) [nM] | Ki [nM] | SD (Ki) [nM] |
| 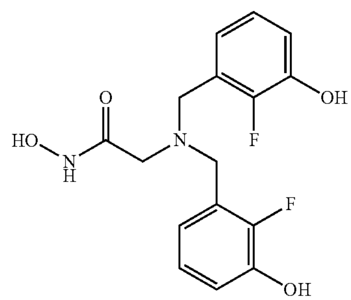 [SMILES: O=C(CN(Cc1cccc(O)c1F)Cc1cccc(O)c1F)NO] | Example 51 | 2905 | 7 | 1170 | 226 | 1210 | 14 | 335 | 3 |
| 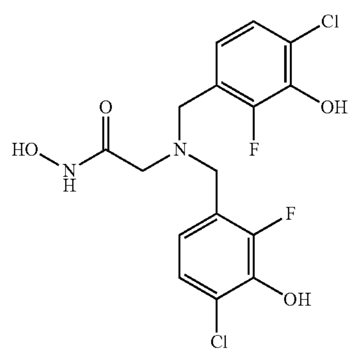 [SMILES: O=C(CN(Cc1ccc(Cl)c(O)c1F)Cc1ccc(Cl)c(O)c1F)NO] | Example 52 | 24 | 1 | 8 | 0.6 | 368 | 8 | 104 | 12 |
| 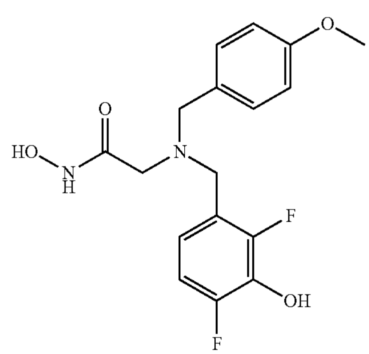 [SMILES: COc1ccc(CN(CC(=O)NO)Cc2ccc(F)c(O)c2F)cc1] | Example 53 | 331 | 4 | 158 | 3 | 995 | 21 | 328 | 28 |
| 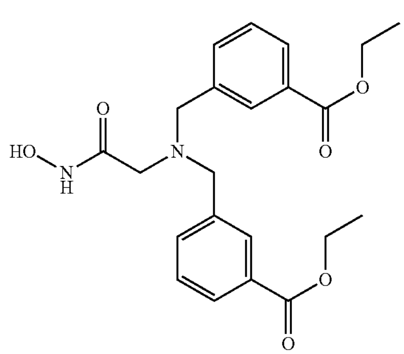 [SMILES: CCOC(=O)c1cccc(CN(CC(=O)NO)Cc2cccc(C(=O)OCC)c2)c1] | Example 54 | 94850 | 10112 | 1755 | 148 | 7270 | 240 | n.d. | n.d. |

TABLE 2-continued

| | | Meprin Beta | | | | Meprin Alpha | | | |
|---|---|---|---|---|---|---|---|---|---|
| Structure | Cpd ID | IC50 [nM] | SD (IC50) [nM] | Ki [nM] | SD (Ki) [nM] | IC50 [nM] | SD (IC50) [nM] | Ki [nM] | SD (Ki) [nM] |
| | Example 55 | n.d. | n.d. | n.d. | n.d. | 5660 | 381 | 1597 | 323 |
| | Example 56 | 12800 | 700 | n.d. | n.d. | 4975 | 35 | 1006 | 91 |
| | Example 57 | 68250 | 1061 | n.d. | n.d. | 3415 | 50 | 1200 | 113 |
| | Example 58 | 18200 | 849 | n.d. | n.d. | 2830 | 57 | 726 | 0.7 |

Compounds of Formula V (Series 4)

TABLE 2-continued

Compounds of Formula V (Series 4)

| Structure | Cpd ID | Meprin Beta | | | | Meprin Alpha | | | |
| --- | --- | --- | --- | --- | --- | --- | --- | --- | --- |
| | | IC50 [nM] | SD (IC50) [nM] | Ki [nM] | SD (Ki) [nM] | IC50 [nM] | SD (IC50) [nM] | Ki [nM] | SD (Ki) [nM] |
| 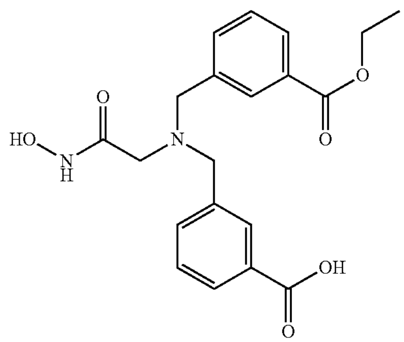 [SMILES: CCOC(=O)c1cccc(CN(CC(=O)NO)Cc2cccc(C(=O)O)c2)c1] | Example 59 | 839 | 30 | 271 | 28 | 4130 | 1598 | 1465 | 148 |
| 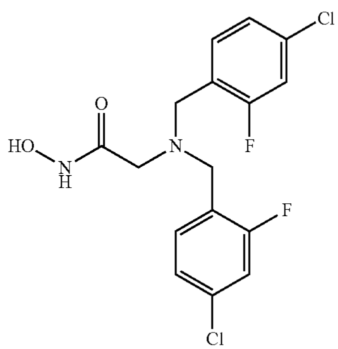 [SMILES: O=C(CN(Cc1ccc(Cl)cc1F)Cc1ccc(Cl)cc1F)NO] | Example 60 | 138000 | 5657 | n.d. | n.d. | 3060 | 198 | 838 | 33 |
| 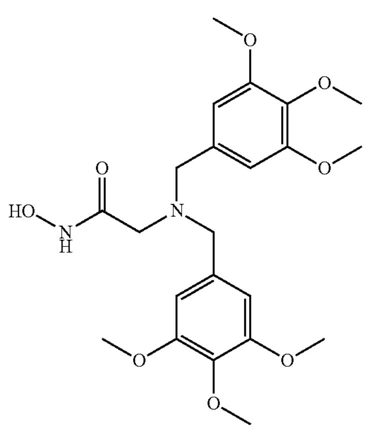 [SMILES: COc1cc(CN(CC(=O)NO)Cc2cc(OC)c(OC)c(OC)c2)cc(OC)c1OC] | Example 61 | 20150 | 354 | n.d. | n.d. | 5320 | 354 | 1180 | 85 |
| 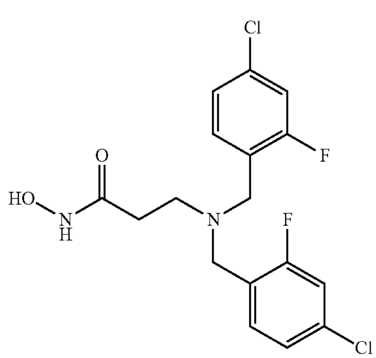 [SMILES: O=C(CCN(Cc1ccc(Cl)cc1F)Cc1ccc(Cl)cc1F)NO] | Example 62 | 19200 | 990 | n.d. | n.d. | 1001 | 41 | 169 | 1 |

TABLE 2-continued

Compounds of Formula V (Series 4)

| Structure | Cpd ID | Meprin Beta | | | | Meprin Alpha | | | |
| --- | --- | --- | --- | --- | --- | --- | --- | --- | --- |
| | | IC50 [nM] | SD (IC50) [nM] | Ki [nM] | SD (Ki) [nM] | IC50 [nM] | SD (IC50) [nM] | Ki [nM] | SD (Ki) [nM] |
| | Example 63 | 30600 | 990 | n.d. | n.d. | 1515 | 35 | 297 | 29 |
| | Example 64 | 18700 | 141 | n.d. | n.d. | 881 | 45 | 332 | 13 |
| | Example 65 | 19600 | 919 | n.d. | n.d. | 495 | 33 | 157 | 30 |
| | Example 66 | 90000 | 4880 | n.d. | n.d. | 19800 | 424 | n.d. | n.d. |

TABLE 2-continued

Compounds of Formula V (Series 4)

| Structure | Cpd ID | Meprin Beta | | | | Meprin Alpha | | | |
|---|---|---|---|---|---|---|---|---|---|
| | | IC50 [nM] | SD (IC50) [nM] | Ki [nM] | SD (Ki) [nM] | IC50 [nM] | SD (IC50) [nM] | Ki [nM] | SD (Ki) [nM] |
| 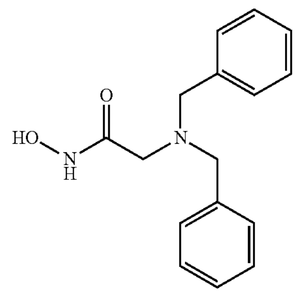 [SMILES: O=C(CN(Cc1ccccc1)Cc1ccccc1)NO] | Example 67 | n.d. | n.d. | n.d. | n.d. | 7880 | 290 | 3090 | 52 |
| 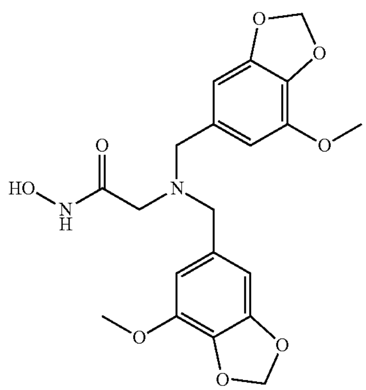 [SMILES: COc1cc(CN(CC(=O)NO)Cc2cc(OC)c3c(c2)OCO3)cc2c1OCO2] | Example 68 | 4570 | 14 | 1820 | 244 | 554 | 25 | 164 | 2 |
| 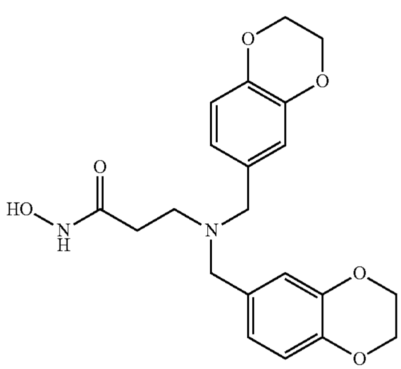 [SMILES: O=C(CCN(Cc1ccc2c(c1)OCCO2)Cc1ccc2c(c1)OCCO2)NO] | Example 69 | 7590 | 14 | 3740 | 42 | 400 | 27 | 117 | 8 |
| 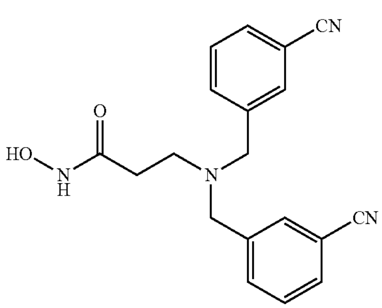 [SMILES: N#Cc1cccc(CN(CCC(=O)NO)Cc2cccc(C#N)c2)c1] | Example 70 | 33100 | 2050 | n.d. | n.d. | 2340 | 35 | 696 | 7 |

TABLE 2-continued

Compounds of Formula V (Series 4)

| | | Meprin Beta | | | | Meprin Alpha | | | |
|---|---|---|---|---|---|---|---|---|---|
| Structure | Cpd ID | IC50 [nM] | SD (IC50) [nM] | Ki [nM] | SD (Ki) [nM] | IC50 [nM] | SD (IC50) [nM] | Ki [nM] | SD (Ki) [nM] |
| (structure) | Example 71 | 75500 | 3680 | n.d. | n.d. | 1680 | 28 | 612 | 12 |
| (structure) | Example 72 | 57000 | 2900 | n.d. | n.d. | 5680 | 325 | 2150 | 107 |
| (structure) | Example 73 | 21700 | 849 | n.d. | n.d. | 1960 | 71 | 637 | 6 |
| (structure) | Example 74 | 2950 | 346 | 1150 | 36 | 150 | 12 | 52 | 1 |

Inhibition of selected other metalloproteases

| Compound ID | Residual enzyme activity @ 200 µM inhibitor | | | | |
|---|---|---|---|---|---|
| | MMP2 | MMP9 | MMP13 | ADAM10 | ADAM17 |
| Example 2 | 64 | 74 | 78 | 93 | 76 |
| Example 6 | 68 | 85 | 94 | 87 | 60 |
| Example 7 | 98 | 92 | 79 | 90 | 71 |
| Example 10 | 74 | 84 | 64 | 94 | 64 |
| Example 11 | 10 | 24 | 7 | 84 | 52 |
| Example 18 | 93 | 85 | 59 | 82 | 60 |
| Example 19 | 50 | 85 | 70 | 98 | 59 |
| Example 20 | 69 | 88 | 78 | 95 | 57 |
| Example 21 | 110 | 96 | 91 | 91 | 64 |
| Example 22 | 62 | 85 | 60 | 91 | 59 |
| Example 31 | 82 | 79 | 50 | 96 | 71 |
| Example 47 | 67 | 94 | 102 | 99 | 82 |
| Example 48 | 87 | 87 | 99 | 92 | 76 |
| Example 52 | 41 | 81 | 93 | 97 | 82 |
| Example 53 | 75 | 73 | 63 | 91 | 59 |

The invention claimed is:

1. A compound, its individual enantiomers, its individual diastereoisomers, its hydrates, its solvates, its crystal forms, its individual tautomers or a pharmaceutically acceptable salt thereof, which is represented by the following Formula V:

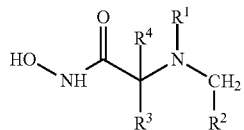

Formula V wherein:

R¹ is joined together with R³ to form a heterocyclic ring;
R² is 3-carboxyphenyl; and
R⁴ is H.

2. A compound represented by the following Formula I, its individual enantiomers, its individual diastereoisomers, its hydrates, its solvates, its crystal forms, its individual tautomers or a pharmaceutically acceptable salt thereof,

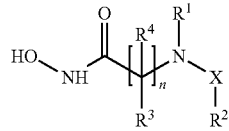

Formula I wherein:
n=1;
R¹ is selected from the group consisting of H and alkyl;
R² is selected the group consisting of 1,3-benzodioxol-5-yl, 3-carboxyphenyl, 4-carboxyphenyl, 3-carboxy-4-methoxyphenyl, 3,5-dichloro-4-hydroxyphenyl, 4-chlorophenyl, 4-cyanophenyl, 4-fluorophenyl, 2,6-difluoro-4-methoxyphenyl, 3-fluoro-4-methoxyphenyl, 3-methoxyphenyl, 4-methoxyphenyl, and 4-methylphenyl;
Each R³ is H;
Each R⁴ is H; and
X is —CH₂—.

3. A compound represented by the following Formula I, its individual enantiomers, its individual diastereoisomers, its hydrates, its solvates, its crystal forms, its individual tautomers or a pharmaceutically acceptable salt thereof,

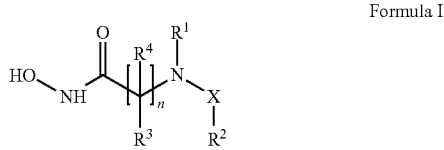

Formula I wherein:

n=1;

R¹ is selected from the group consisting of H and alkyl; wherein said alkyl may be joined together with R³ to form a ring;

R² is 3-carboxyphenyl;

R³ is independently selected from the group consisting of H, methyl, ethyl, 1-propyl, 2 propyl, aryl, arylalkyl, heteroaryl, heteroarylalkyl, and 2-carboxyethyl; and each of said arylalkyl, heteroaryl, and heteroarylalkyl can be optionally substituted;

R⁴ is H; and

X is —CH₂—.

4. A compound, its individual enantiomers, its individual diastereoisomers, its hydrates, its solvates, its crystal forms, its individual tautomers or a pharmaceutically acceptable salt thereof, selected from the group consisting of:

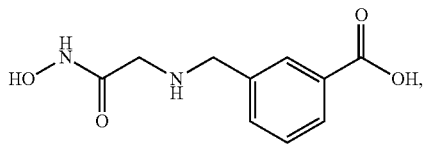

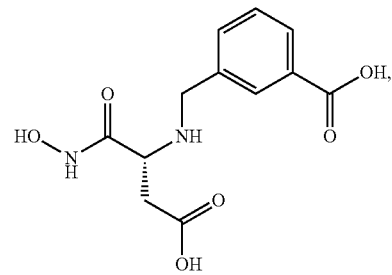

93
-continued
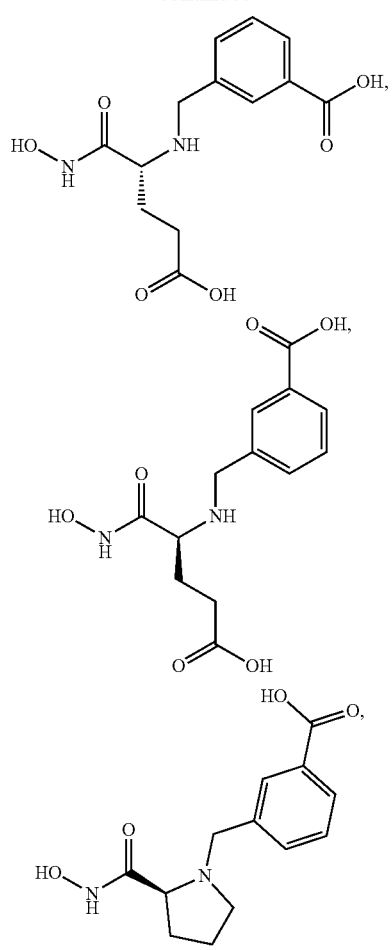
94
-continued
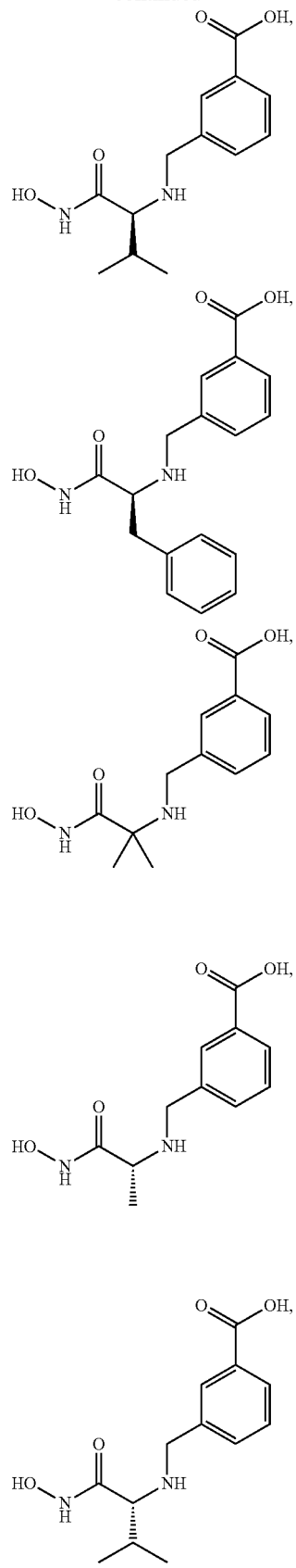

-continued

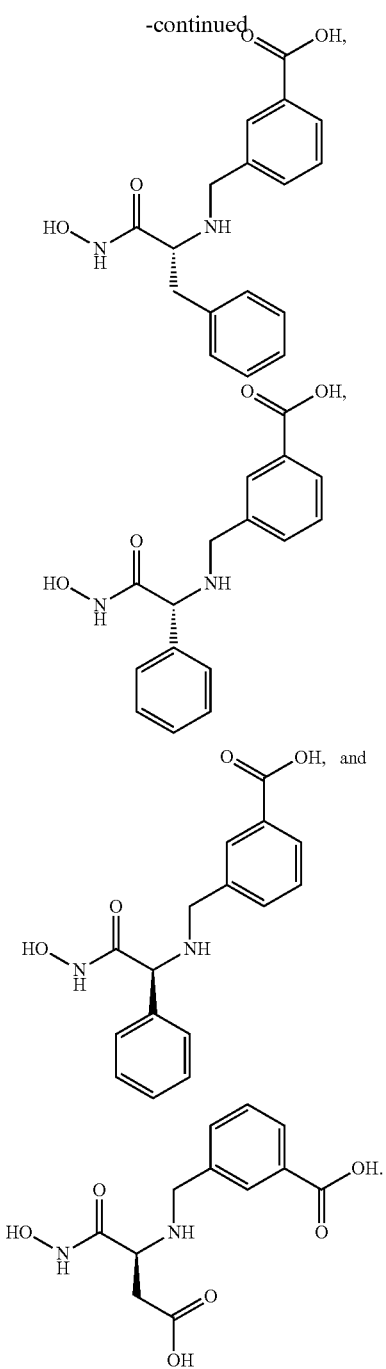

5. A pharmaceutical composition comprising:
the compound according to claim 2, its individual enantiomers, its individual diastereoisomers, its hydrates, its solvates, its crystal forms, its individual tautomers or a pharmaceutically acceptable salt thereof; and a pharmaceutically acceptable excipient.

6. A method for treatment or prophylaxis of the human or animal body by surgery or therapy comprising administering a therapeutically effective amount of a compound, its individual enantiomers, its individual diastereoisomers, its hydrates, its solvates, its crystal forms, its individual tautomers or a pharmaceutically acceptable salt thereof, according to claim 2 to a subject in need thereof.

7. A method for treatment or prophylaxis of a disease or condition selected from Alzheimer's disease, nephritis, renal injury, renal ischemic injury, ischemic acute tubular necrosis, acute renal failure, bladder inflammation, inflammatory bowel disease (IBD), Crohn's disease, ulcerative colitis, chronic inflammation, colitis, fibrosis, fibrotic conditions, keloids, pulmonary hypertension, interstitial lung disease (ILD), cancer, and colorectal cancer, the method comprising administering a therapeutically effective amount of a compound, its individual enantiomers, its individual diastereoisomers, its hydrates, its solvates, its crystal forms, its individual tautomers or a pharmaceutically acceptable salt thereof, according to claim 2 to a subject in need thereof.

8. A method for treatment or prophylaxis of the human or animal body by surgery or therapy comprising administering a therapeutically effective amount of a pharmaceutical composition according to claim 5 to a subject in need thereof.

9. A method for treatment or prophylaxis of a disease or condition selected from Alzheimer's disease, nephritis, renal injury, renal ischemic injury, ischemic acute tubular necrosis, acute renal failure, bladder inflammation, inflammatory bowel disease (IBD), Crohn's disease, ulcerative colitis, chronic inflammation, colitis, fibrosis, fibrotic conditions, keloids, pulmonary hypertension, interstitial lung disease (ILD), cancer, and colorectal cancer, the method comprising administering a therapeutically effective amount of a pharmaceutical composition according to claim 5 to a subject in need thereof.

10. A pharmaceutical composition comprising:
a compound represented by the following Formula I, its individual diastereoisomers, its hydrates, its solvates, its crystal forms, its individual tautomers or a pharmaceutically acceptable salt thereof; and a pharmaceutically acceptable excipient;

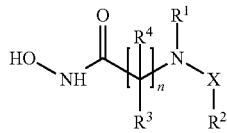

Formula I wherein:
$n=1$;
$R^1$ is selected from the group consisting of H and alkyl; wherein said alkyl may be joined together with $R^3$ to form a ring;
$R^2$ is 3-carboxyphenyl;
$R^3$ is independently selected from the group consisting of H, $C_{1-4}$alkyl, aryl, arylalkyl, heteroaryl, and heteroarylalkyl; each of which can be optionally substituted; wherein said alkyl may be joined together with $R^1$ to form a ring;
$R^4$ is H; and
X is $-CH_2-$.

11. A method for treatment or prophylaxis of the human or animal body by surgery or therapy comprising administering a therapeutically effective amount of a compound, its individual enantiomers, its individual diastereoisomers, its hydrates, its solvates, its crystal forms, its individual tautomers or a pharmaceutically acceptable salt thereof, according to claim 3 to a subject in need thereof.

12. A method for treatment or prophylaxis of a disease or condition selected from Alzheimer's disease, nephritis, renal injury, renal ischemic injury, ischemic acute tubular necrosis, acute renal failure, bladder inflammation, inflammatory bowel disease (IBD), Crohn's disease, ulcerative colitis, chronic inflammation, colitis, fibrosis, fibrotic conditions, keloids, pulmonary hypertension, interstitial lung disease (ILD), cancer, and colorectal cancer, the method comprising administering a therapeutically effective amount of a compound, its individual enantiomers, its individual diastereoisomers, its hydrates, its solvates, its crystal forms, its individual tautomers or a pharmaceutically acceptable salt thereof, according to claim 3 to a subject in need thereof.

13. A method for treatment or prophylaxis of the human or animal body by surgery or therapy comprising administering a therapeutically effective amount of a pharmaceutical composition according to claim 10 to a subject in need thereof.

14. A method for treatment or prophylaxis of a disease or condition selected from Alzheimer's disease, nephritis, renal injury, renal ischemic injury, ischemic acute tubular necrosis, acute renal failure, bladder inflammation, inflammatory bowel disease (IBD), Crohn's disease, ulcerative colitis, chronic inflammation, colitis, fibrosis, fibrotic conditions, keloids, pulmonary hypertension, interstitial lung disease (ILD), cancer, and colorectal cancer, the method comprising administering a therapeutically effective amount of a pharmaceutical composition according to claim 10 to a subject in need thereof.

15. A pharmaceutical composition comprising:
   the compound according to claim 4, its individual enantiomers, its individual diastereoisomers, its hydrates, its solvates, its crystal forms, its individual tautomers or a pharmaceutically acceptable salt thereof; and a pharmaceutically acceptable excipient.

16. A method for treatment or prophylaxis of the human or animal body by surgery or therapy comprising administering a therapeutically effective amount of a compound, its individual enantiomers, its individual diastereoisomers, its hydrates, its solvates, its crystal forms, its individual tautomers or a pharmaceutically acceptable salt thereof, according to claim 4 to a subject in need thereof.

17. A method for treatment or prophylaxis of a disease or condition selected from Alzheimer's disease, nephritis, renal injury, renal ischemic injury, ischemic acute tubular necrosis, acute renal failure, bladder inflammation, inflammatory bowel disease (IBD), Crohn's disease, ulcerative colitis, chronic inflammation, colitis, fibrosis, fibrotic conditions, keloids, pulmonary hypertension, interstitial lung disease (ILD), cancer, and colorectal cancer, the method comprising administering a therapeutically effective amount of a compound, its individual enantiomers, its individual diastereoisomers, its hydrates, its solvates, its crystal forms, its individual tautomers or a pharmaceutically acceptable salt thereof, according to claim 4 to a subject in need thereof.

18. A method for treatment or prophylaxis of the human or animal body by surgery or therapy comprising administering a therapeutically effective amount of a pharmaceutical composition according to claim 15 to a subject in need thereof.

19. A method for treatment or prophylaxis of a disease or condition selected from Alzheimer's disease, nephritis, renal injury, renal ischemic injury, ischemic acute tubular necrosis, acute renal failure, bladder inflammation, inflammatory bowel disease (IBD), Crohn's disease, ulcerative colitis, chronic inflammation, colitis, fibrosis, fibrotic conditions, keloids, pulmonary hypertension, interstitial lung disease (ILD), cancer, and colorectal cancer, the method comprising administering a therapeutically effective amount of a pharmaceutical composition according to claim 15 to a subject in need thereof.

\* \* \* \* \*

SEQUENCE LISTING

```
<160> NUMBER OF SEQ ID NOS: 4

<210> SEQ ID NO 1
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: Xaa corresponds to Lys modified with Dnp
      (2,4-dinitrophenyl)

<400> SEQUENCE: 1

Tyr Val Ala Glu Ala Pro Xaa Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: Xaa corresponds to Lys modified with Dnp
      (2,4-dinitrophenyl)

<400> SEQUENCE: 2

Tyr Val Ala Asp Ala Pro Xaa Gly
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (5)..(5)
<223> OTHER INFORMATION: Xaa corresponds to DprDnp, i.e. Dpr
      (2,3-diaminopropionic acid) modified with Dnp (2,4-dinitrophenyl)

<400> SEQUENCE: 3

Pro Leu Gly Leu Xaa Ala Arg
1               5

<210> SEQ ID NO 4
<211> LENGTH: 11
<212> TYPE: PRT
```

```
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (11)..(11)
<223> OTHER INFORMATION: Xaa corresponds to DprDnp, i.e. Dpr
      (2,3-diaminopropionic acid) modified with Dnp (2,4-dinitrophenyl)

<400> SEQUENCE: 4

Leu Ala Asn Ala Val Arg Ser Ser Ser Arg Xaa
1               5                   10
```